(12) United States Patent
Masters et al.

(10) Patent No.: US 8,529,939 B2
(45) Date of Patent: Sep. 10, 2013

(54) MUCOADHESIVE DRUG DELIVERY DEVICES AND METHODS OF MAKING AND USING THEREOF

(75) Inventors: David B. Masters, Minneapolis, MN (US); Eric P. Berg, Plymouth, MN (US)

(73) Assignee: Gel-Del Technologies, Inc., St. Paul, MN (US)

( * ) Notice: Subject to any disclaimer, the term of this patent is extended or adjusted under 35 U.S.C. 154(b) by 945 days.

(21) Appl. No.: 11/007,053

(22) Filed: Dec. 8, 2004

(65) Prior Publication Data

US 2005/0196440 A1 Sep. 8, 2005

Related U.S. Application Data

(60) Provisional application No. 60/527,962, filed on Dec. 8, 2003.

(51) Int. Cl.
  *A61K 39/08* (2006.01)
  *A61K 39/12* (2006.01)
  *A61K 9/20* (2006.01)
  *A61K 38/00* (2006.01)
  *A61K 48/00* (2006.01)
  *A61K 31/557* (2006.01)

(52) U.S. Cl.
  USPC ........... 424/434; 424/435; 424/484; 424/499; 514/15.5

(58) Field of Classification Search
  USPC ....................... 426/531; 424/1.29
  See application file for complete search history.

(56) References Cited

U.S. PATENT DOCUMENTS

| | | | |
|---|---|---|---|
| 3,800,792 A | 4/1974 | McKnight | |
| 3,996,934 A | 12/1976 | Zaffaroni | 424/434 |
| 4,226,848 A | 10/1980 | Nagai | 514/772.1 |
| 4,250,163 A | 2/1981 | Nagai | 514/772.1 |
| 4,286,592 A | 9/1981 | Chandrasekaran | 424/448 |
| 4,292,299 A | 9/1981 | Suzuki | 424/435 |
| 4,347,234 A | 8/1982 | Wahlig | 424/426 |
| 4,352,883 A | 10/1982 | Lim | 435/178 |
| 4,394,370 A | 7/1983 | Jefferies | 606/76 |
| 4,405,311 A | 9/1983 | Greatbatch | 604/20 |
| 4,438,253 A | 3/1984 | Casey | |
| 4,474,752 A | 10/1984 | Haslam | 424/78 |
| 4,517,173 A | 5/1985 | Kizawa | 424/435 |
| 4,518,721 A | 5/1985 | Dhabhar | 523/120 |
| 4,526,938 A | 7/1985 | Churchill | |
| 4,553,545 A | 11/1985 | Maass | 606/198 |
| 4,572,832 A * | 2/1986 | Kigasawa et al. | 514/772.1 |
| 4,596,574 A | 6/1986 | Urist | 424/422 |
| 4,600,533 A | 7/1986 | Chu | 530/356 |
| 4,652,441 A | 3/1987 | Okada | |
| 4,706,680 A | 11/1987 | Keusch | 600/392 |
| 4,713,243 A | 12/1987 | Schiraldi | 424/676 |
| 4,733,665 A | 3/1988 | Palmaz | |
| 4,739,762 A | 4/1988 | Palmaz | |
| 4,741,872 A | 5/1988 | De Luca | 264/4.7 |
| 4,780,450 A | 10/1988 | Sauk | 514/2 |
| 4,800,882 A | 1/1989 | Gianturco | 606/194 |
| 4,801,299 A | 1/1989 | Brendel | |
| 4,849,141 A | 7/1989 | Fujioka | |
| 4,894,232 A | 1/1990 | Reul | 424/439 |
| 4,900,554 A | 2/1990 | Yanagibashi | 424/448 |
| 4,907,336 A | 3/1990 | Gianturco | |
| 4,915,948 A | 4/1990 | Gallopo | 424/435 |
| 4,917,161 A | 4/1990 | Townend | 131/352 |
| 4,959,217 A | 9/1990 | Sanders | 424/473 |
| 5,019,372 A | 5/1991 | Folkman | 424/422 |
| 5,035,706 A | 7/1991 | Gianturco | |
| 5,037,392 A | 8/1991 | Hillstead | |
| 5,041,126 A | 8/1991 | Gianturco | |
| 5,041,292 A | 8/1991 | Feijen | 424/484 |
| 5,100,669 A | 3/1992 | Hyon | |
| 5,102,417 A | 4/1992 | Palmaz | |
| 5,137,729 A | 8/1992 | Kuroya | 424/435 |
| 5,145,702 A * | 9/1992 | Stark et al. | 426/531 |
| 5,147,385 A | 9/1992 | Beck | |
| 5,166,187 A | 11/1992 | Collombel | 514/21 |
| 5,188,837 A | 2/1993 | Domb | 424/450 |
| 5,192,802 A | 3/1993 | Rencher | 514/535 |
| 5,282,824 A | 2/1994 | Gianturco | |
| 5,298,258 A | 3/1994 | Akemi | 424/484 |

(Continued)

FOREIGN PATENT DOCUMENTS

| | | |
|---|---|---|
| CA | 1239755 | 8/1988 |
| CA | 1245527 | 11/1988 |

(Continued)

OTHER PUBLICATIONS

Puri et al., "Adjuvancy enhancement of muramyl dipeptide by modulatin its release from a physicochemically modified matrix of ovalbumin micorpsheres I. In vitro chracterization." Journal of Controlled Release 2000:69;63-67.*

Mellon et al., "Water Absorption of Proteins. IV. Effect of Physical Structure." Journal of the American Chemical Society 1949: 71;2761-2764.*

Bredenberg et al., "In-vitro evaluation of bioadhesion in particulate systems and possible improvement using interactive mixtures." Pharmacy and Pharmacology 2003:55;169-177.*

Hancock, "Peptide Antibiotics". Lancet 1997:349;418-22.*

US 5,679,669, 10/1997, Colvard (withdrawn).

Anderson "Morphology and Primary Crystal Structure of a Silk-like Protein Polymer Synthesized by Genetically Engineered *Escherichia coli* Bacteria", *Biopolymers*, New York, NY, vol. 34, No. 8, Aug. 1, 1994, pp. 1049-1058.

(Continued)

*Primary Examiner* — Walter Webb
(74) *Attorney, Agent, or Firm* — Patterson Thuente Pedersen, P.A.

(57) ABSTRACT

The present invention relates to mucoadhesive drug delivery devices and their methods of preparation and use. More specifically the present invention relates to mucoadhesive drug delivery devices comprising one or more biocompatible purified proteins combined with one or more biocompatible solvents and one or more mucoadhesive agents. The mucoadhesive drug delivery devices may also include one or more pharmacologically active agents. The drug delivery devices of the present invention adhere to mucosal tissue, thereby providing a vehicle for delivery of the pharmacologically active agent(s) through such tissue.

40 Claims, 5 Drawing Sheets

(56) References Cited

U.S. PATENT DOCUMENTS

| | | | |
|---|---|---|---|
| 5,314,915 A | 5/1994 | Rencher | 514/535 |
| 5,316,023 A | 5/1994 | Palmaz | |
| 5,324,261 A * | 6/1994 | Amundson et al. | 604/103.02 |
| 5,324,775 A | 6/1994 | Ree | 525/54.2 |
| 5,330,768 A | 7/1994 | Park | |
| 5,385,606 A * | 1/1995 | Kowanko | 106/156.3 |
| 5,418,222 A | 5/1995 | Song | |
| 5,423,739 A | 6/1995 | Phipps | 604/20 |
| 5,431,921 A * | 7/1995 | Thombre | 424/424 |
| 5,443,483 A | 8/1995 | Kirsch | |
| 5,447,940 A | 9/1995 | Harvey | |
| 5,487,895 A | 1/1996 | Dapper | 424/278.1 |
| 5,510,077 A | 4/1996 | Dinh | 264/485 |
| 5,512,291 A | 4/1996 | Li | 424/443 |
| 5,518,502 A * | 5/1996 | Kaplan et al. | 600/157 |
| 5,573,934 A | 11/1996 | Hubbell | 435/177 |
| 5,607,445 A | 3/1997 | Summers | 623/1.22 |
| 5,642,749 A | 7/1997 | Perryman | 135/66 |
| 5,665,428 A | 9/1997 | Cha | 427/213.3 |
| 5,676,699 A | 10/1997 | Gogolewski | 623/16.11 |
| 5,700,478 A | 12/1997 | Cha | 427/213 |
| 5,709,683 A | 1/1998 | Bagby | |
| RE35,748 E | 3/1998 | Luck | |
| 5,741,670 A | 4/1998 | Goetinck | |
| 5,773,019 A | 6/1998 | Ashton | 424/423 |
| 5,783,214 A | 7/1998 | Royer | |
| 5,834,232 A | 11/1998 | Bishop | |
| 5,863,554 A | 1/1999 | Illum | |
| 5,879,713 A * | 3/1999 | Roth et al. | 424/489 |
| 5,948,427 A | 9/1999 | Yamamoto | 424/426 |
| 5,981,568 A | 11/1999 | Kunz | 514/411 |
| 6,004,943 A | 12/1999 | Shi | |
| 6,007,791 A * | 12/1999 | Coombes et al. | 424/1.29 |
| 6,074,689 A | 6/2000 | Luck | 427/2.21 |
| 6,179,834 B1 | 1/2001 | Buysse | 606/41 |
| 6,210,429 B1 | 4/2001 | Vardi | 623/1.11 |
| 6,248,110 B1 | 6/2001 | Reiley | |
| 6,287,765 B1 | 9/2001 | Cubicciotti | |
| 6,291,582 B1 | 9/2001 | Dordick | |
| 6,342,250 B1 | 1/2002 | Masters | |
| 6,371,988 B1 | 4/2002 | Pafford | |
| 6,592,891 B1 * | 7/2003 | Donati et al. | 424/448 |
| 6,960,452 B2 | 11/2005 | Hubbell | |
| 2001/0008636 A1 | 7/2001 | Yamamoto | 424/426 |
| 2001/0020086 A1 | 9/2001 | Hubbell | 530/322 |
| 2002/0028243 A1 * | 3/2002 | Masters | 424/484 |
| 2002/0052572 A1 | 5/2002 | Franco | 623/1.11 |
| 2002/0065553 A1 | 5/2002 | Weber | 606/1 |
| 2002/0141945 A1 | 10/2002 | Foster | |
| 2003/0007991 A1 | 1/2003 | Masters | |
| 2003/0028204 A1 | 2/2003 | Li | 606/152 |
| 2003/0215515 A1 | 11/2003 | Truong-Le | |
| 2004/0002558 A1 | 1/2004 | McKay | 623/23 |
| 2005/0147690 A1 | 7/2005 | Masters | |
| 2006/0210601 A1 | 9/2006 | Yunoki | 514/12 |

FOREIGN PATENT DOCUMENTS

| | | |
|---|---|---|
| CA | 2085255 | 12/1991 |
| CA | 2134997 | 5/1996 |
| CA | 2239775 | 6/1997 |
| CA | 2171047 | 9/1997 |
| CA | 2192520 | 9/1997 |
| CA | 2175722 | 11/1997 |
| CA | 2251129 | 11/1997 |
| CA | 2185740 | 3/1998 |
| CA | 2290806 | 12/1998 |
| EP | 0224934 | 6/1987 |
| EP | 0 258 780 A2 | 8/1987 |
| EP | 0485210 | 5/1992 |
| EP | 0518697 | 12/1992 |
| EP | 0 567 234 A1 | 3/1993 |
| EP | 0 636 378 B1 | 7/1994 |
| WO | 93/24150 A1 | 12/1993 |
| WO | 97/32543 A1 | 9/1997 |
| WO | 97/32544 A1 | 9/1997 |
| WO | 97/41803 A1 | 11/1997 |
| WO | 9741899 | 11/1997 |
| WO | 99/32613 A1 | 7/1999 |
| WO | WO9932107 | 7/1999 |
| WO | 9938546 | 8/1999 |
| WO | 9949907 | 10/1999 |
| WO | 0119305 | 3/2001 |
| WO | WO0128524 | 4/2001 |
| WO | 0183522 A2 | 11/2001 |
| WO | 0187267 A1 | 11/2001 |
| WO | WO02058735 | 8/2002 |

OTHER PUBLICATIONS

Bradley "Some mechanical property considerations of reconstituted collagen for drug release supports", *Biomaterials, Medical Devices, and Artificial Organs*, 1997, vol. 5, No. 2, pp. 159-175.

Cappello "In situ self-assembling protein polymer gel systems for administration, delivery and release of drugs", *Journal of controlled Release*, Elsevier, Amsterdam, NL, vol. 53, No. 1-3, Apr. 30, 1998, pp. 105-117.

Ferrari "Biosynthesis of Protein Polymers", *Protein-Based Materials*, 1997, pp. 37-60.

Foscolo "Full Length article" Biofutur. Le Mensuel Europeen De Biotechnology, Lavoisier, Cachan, FR vol. 1997 (Oct. 1997), pp. 14-17.

*Handbook of Food Science, Technology and Engineering.* Yiu, Hu H. (editor), 2006, CRC Press.

Lee, J. *Controlled Release*, 2, 227 (1985).

Masters, Letter to Joseph Cappello, Jul. 1, 1996.

Masters, Improvements in Perineural Local Anesthetic Block, Abstract, CRISP—Computer Retrieval of Information on Scientific Projects, printed Sep. 22, 1998.

Polymeric Materials Encyclopedia. Salamone, J.C. (editor), 1996, *CRC Press*. (see p. 7451).

Http://www.merriam-webster.com/dictionary/binding (accessed Jan. 24, 2009).

AAPS: Annual Meeting & Exposition, *Symposia Abstracts & Biographies*, Boston, MA, Nov. 2, 1997, pp. 25-27.

Abbott, et al., *Vascular Grafts: Characteristics and Routine Selection of Prostheses*, Vascular Surgery, a Comprehensive Review, 5th Edition, (Pub . Oct. 1997).

Abstracts, *Eighth International Symposium on Recent Advances in Drug Delivery Systems*, Feb. 24, 1997, Salt Lake City, UT, pp. 36-39, 138-140.

*American Red Cross Open to Partners for New Fibrin Sealant*, Genetic Engineering News, Mar. 1995, p. 30.

Anderson, *Characterization of Silk-like Proteins and Processing for Biomedical Applications*, Protein-Based Materials, 1997, pp. 371-423.

*The Biological Production of Protein Polymers and Their Use*, Trends in Biotechnology, Nov. 1990, vol. 8, No. 11.

Cappello, et al., *Microbial Production of Structural Polymers*, (ed. Mobley), 1994 Carl Hanser Verlag, Munich, pp. 35-92.

Cappello, et al., *Genetic Engineering of Structural Protein Polymers*, Biotechnology Progress, 1990, pp. 198-202.

Cappello, *Protein Engineering for Biomaterials Applications*, Current Opinion in Structural Biology, 1992, 2:582-586.

Caruana, *New Drugs Spur Novel Delivery Systems*, Chemical Engineering Progress, Jul. 1997, pp. 15-19.

Choi, et al. Implantation Biology: The Host Response and Biomedical Devices. *The Effect of Biomaterials on the Host*, CRC Press, Boca Raton 405 pages, 1994. Chapter. 3, pp. 39-53.

Chvapil, et al., *Some Chemical and Biological Characteristics of a New Collagen-Polymer\* Compound Material*, J. Biomed. Mater. Res. vol. 3, pp. 315-331 (1969).

Davis, et al., *Chemically Cross-Linked Albumin Microspheres for the Controlled Release of Incorporated Rose Bengal After Intramuscular Injection Into Rabbits*, Journal of Controlled Release, 4 (1987) 293-302.

Dickinson, et al., *Biodegradation of a poly(α-amino acid) hydrogel. I*. In vivo, Journal of Biomedical Materials Research, vol. 15, 577-589 (1981).

Drug Delivery Systems (Program), Feb. 1998, San Francisco.

Dunn, et al., *Biomaterials Used in Orthopaedic Surgery*, Implantation Biology, CRC Press, Boca Raton, 1994, pp. 229-252.

Dutton, *Tissue Engineering: Continued Growth Expected as New Techniques Evolve*, Genetic Engineering News, Apr. 1998, pp. 21, 37.

Fernandes, et al., *Regulation of Polymeric Implants for Site-specific Drug Delivery*, Polymeric Site-specific Pharmcotherapy, Chapter 16, pp. 424-441, (Pub. Jul. 26, 1994).

Ghandehari, et al., *Genetic Engineering of Protein-Based Polymers: Potential in Controlled Drug Delivery*, Pharmaceutical Research, vol. 15, No. 6, 1998, pp. 813-815.

Harvey, *Utilizing Prostheses for Drug Delivery*, Implantation Biology, CRC Press, Boca Raton, 1994, pp. 329-345.

Heller, et al., *Controlled release of water-soluble macromolecules from Bioerodible Hydrogels*, Biomaterials 1983, vol. 4 October pp. 262-266.

Kelly, *Researchers Advancing Biopolymer Systems as Vehicles for Delivering Drugs*, Genetic Engineering News, May 15, 1997, pp. 1, 25, 32, 35, 36, 41.

Langer, *1994 Whitaker Lecture: Polymers for Drug Delivery and Tissue Engineering*, Annals of Biomedical Engineering, 1995, vol. 23, pp. 101-111.

Lewis, *New Directions in Research on Blood Substitutes*, Genetic Engineering News, Jun. 15, 1997, pp. 1, 10, 12, 20, 26, 33, 35, 36, 41.

Li, et al, *A Novel Biodegradable System Based on Gelatin Nanoparticles and Poly(lactic-co-glycolic acid) Microspheres for Protein and Peptide Drug Delivery*, Journal of Pharmaceutical Sciences, vol. 86, No. 8, Aug. 1997, p. 891-895.

Masters, et al., *Liposphere Local Anesthetic Timed-Release for Perineural Site Application*, Pharmaceutical Research, vol. 15, No. 7, 1998, pp. 1038-1045.

Masters, et al., *Sustained Local Anesthetic Relapse from Bioerodible Polymer Matrices: A Potential Method for Prolonged Regional Anesthesia*, Pharmaceutical Research, vol. 10, No. 10, 1993, pp. 1527-1532.

Masters, Course Syllabus for Mayo Graduate Course, *Polymeric Site-Specific Drug Delivery*, Apr. 1998.

Masters, et al., *Prolonged Regional Nerve Blockade by Controlled Release of Local Anesthetic from a Biodegradable Polymer Matrix*, Anesthesiology, vol. 79, No. 2, 1993, pp. 340-346.

Masters, *Drug Delivery to Peripheral Nerves*, Polymeric Site-Specific Pharmacotherapy, 1994, pp. 443-455.

Morrow, *Companies to Take Broad Range of Approaches to Develop Rheumatoid Arthritis Therapies*, Genetic Engineering News, Jan. 15, 1997, pp. 1, 7, 9, 24.

Ohtani, *Three-Dimensional Organization of the Collagen Fibrillar Framework of the Human and Rat Livers*, Arch. Hist. Cytol., vol. 51, No. 5, 1988, pp. 473-788.

Peppas, et al. *New Challenges in Biomaterials*, Science, Mar. 1994, vol. 263, pp. 1715-1720.

Pramik, *Drug Delivery Firms Focus on Controlled Release Techniques*, Genetic Engineering News, Oct. 1, 1996, pp. 1, 38, 40.

Pramik, *Positive Clinical Results in Pulmonary Drug Delivery: Inhaled Insulin Effective as Injected Drug*, Genetic Engineering News, Jul. 1998, vol. 18, No. 13, pp. 1, 12, 35, 46.

Protein Polymer Technologies: 1994 Annual Report, *BioEngineered Tissue Repair and Regeneration*.

R&D, A Cahners Publication, *BioDerived Materials*, Jun. 1990, p. 58.

Ranade, *Drug Delivery Systems: 3A. Role of Polymers in Drug Delivery*, J.Clin. Pharmacol 1990; 30: 10-23.

Ranade, *Drug Delivery Systems: 3A. Role of Polymers in Drug Delivery*, J.Clin. Pharmacol 1990; 30: 107-120.

Ratner, et al., *An Introduction to Materials in Medicine*, Biomaterials Science, 1996.

Sedlak, *Hyal Pharmaceutical Looks for Home Run with HIT Drug Delivery System*, Genetic Engineering News, Sep. 1, 1995, p. 16.

Sedlak, *Signal Transduction Companies Moving Some Products to the Clinical Testing Environment*, Genetic Engineering News, Mar. 15, 1997, vol. 17, No. 6, pp. 1, 27, 36.

Skarda, et al., *Biodegradable Hydrogel for Controlled Release of Biologically Active Macromolecules*, Journal of Bioactive and Compatible Polymers, vol. 8, Jan. 1993, pp. 24-40.

*Tissue Engineering*, Genetic Engineering News, Jan. 1998, p. 33.

Urry, et al., *Protein-Based Materials with a Profound Range of Properties and Applications: The Elastin $\Delta T_t$ Hydrophobic Paradigm*, Protein-Based Materials, 1997, pp. 133-177.

\* cited by examiner

MUCOADHESIVE DRUG DELIVERY DEVICES AND METHODS OF MAKING AND USING THEREOF

FIELD OF THE INVENTION

The present invention relates to mucoadhesive drug delivery devices and their methods of preparation and use. More specifically the present invention relates to mucoadhesive drug delivery devices comprising one or more biocompatible purified proteins combined with one or more biocompatible solvents and one or more mucoadhesive agents. The mucoadhesive drug delivery devices may also include one or more pharmacologically active agents. The drug delivery devices of the present invention adhere to mucosal tissue, thereby providing a vehicle for delivery of the pharmacologically active agent(s) through such tissue.

BACKGROUND OF THE INVENTION

The localized and systemic delivery of pharmacologically active agents for treatment of body tissues, diseases, and wounds requires that for proper absorption of the particular pharmaceutical component, the drug delivery device be maintained at the site of administration for an effective period of time. Given the tendency of natural bodily fluids to clear applied pharmaceutical components from the site of administration, the administration of drugs to wet mucosal tissues located in body sites, such as buccal, sublingual, palate, nasal, vaginal, anal, urethral, stomach, intestinal or pulmonary areas, have been problematic. For example, in the mouth, saliva, natural replacement of the mucosal tissue, eating, drinking, and speaking movements are some of the problems that have limited the effectiveness and residence time of pharmaceutical carriers.

Various benefits can be obtained through delivery of pharmacologically active agents through the mucosal tissue. For example, mucosal drug delivery is generally noninvasive, thereby avoiding the uncomfortable aspects of intravenous, intramuscular, or subcutaneous delivery means. Furthermore, mucosal drug delivery device attachment protects the pharmacologically active agents from clearance from the drug absorption site, thereby increasing the bioavailability of the drug.

Many theories have been proposed to describe mucoadhesion, namely electronic theory, adsorption theory, wetting theory, diffusion theory and fracture theory. Mucoadhesion is believed to occur in three stages: wetting, interpenetration and mechanical interlocking between mucin and the mucoadhesive substance. According to electronic theory, mucoadhesion occurs from the formation of an electric double layer at the mucoadhesive interface by the transfer of electrons between the mucoadhesive substance and the mucin glycoprotein network. Adsorption theory states that mucoadhesive systems adhere to tissue through secondary molecular interactions such as van der Waals forces and hydrogen bonding. Intimate molecular contact is a prerequisite for the development of strong adhesive bonds, whereby wetting equilibrium and the dynamic behavior of the bioadhesive substance with the mucus is critical. The interfacial energetics is responsible for the contact of the two surfaces and the adhesive strength. Further, diffusion theory states that interpenetration of the bioadhesive substance and mucus may lead to sustained mucoadhesion and by mechanical interlocking between mucin and mucoadhesives. It is noted that additional explanations for mucoadhesion may also exist.

Bioadhesive carriers are known in the art and include gels, pastes, tablets, and films. These products, however, may lack one or several of the preferred characteristics for an efficient and commercially acceptable pharmaceutical delivery device. Some characteristics which are preferred by users of bioadhesive carriers include controlled water-erodability, ease of handling and application to the delivery/treatment site, and ease of comfort, with minimal foreign body sensation. Other preferred characteristics for an effective and user-friendly product for administration to mucosal surfaces include the use of pharmaceutically approved components or materials; instantaneous adhesion to mucosal surface upon application; and increased residence time for the protection of the affected tissue or the delivery of the pharmaceutical component for enhanced absorption.

Bioadhesive gels which are used for application to mucosal tissues and especially the oral cavity are known in the art. For example, U.S. Pat. No. 5,192,802 describes a bioadhesive teething gel made from a blend of sodium carboxymethyl cellulose and xantham gum. The gel may also have potential use in the treatment of canker sores, fever blisters, and hemorrhoids. However, this type of pharmaceutical carrier has a very limited residence time, given that body fluids such as saliva quickly wash it away from the treatment site. Bioadhesive gels are also described in U.S. Pat. Nos. 5,314,915; 5,298,258; and 5,642,749. The gels described in those patents use an aqueous or oily medium and different types of bioadhesive and gelling agents.

Denture adhesive pastes are another type of bioadhesive product known in the art. However, these preparations are used primarily for their adhesive properties, to adhere dentures to the gums, rather than for the protection of tissue or for the topical delivery of pharmaceuticals, although drugs such as local anesthetics may be used in the paste for the relief of sore gums. U.S. Pat. Nos. 4,894,232 and 4,518,721 describe denture adhesive pastes. The '721 Patent describes a combination of sodium carboxymethyl cellulose and polyethylene oxide in polyethylene glycol.

Pastes have also been used as film protectants and as drug delivery systems. One such example having film forming and adhesive properties is the product commercialized under the name Orabase®, which is a thick gel or paste for the relief of mouth sores. Ingredients include guar gum, sodium carboxymethyl cellulose, tragacanth gum, and pectin. Even though it does provide numbing to the area of application, the film forming behavior and bioadhesion do not last. Thus, this product has a limited residence time.

Bioadhesive tablets are described in U.S. Pat. No. 4,915,948. The water-soluble bioadhesive material used in this device is a xanthan gum or a pectin combined with an adhesion enhancing material such as a polyol. Although residence time is improved with the use of bioadhesive tablets, they are not user friendly, especially when used in the oral cavity, given the unpleasant feelings associated with their solidity, bulkiness, and slow dissolution time. Bioadhesive tablets are also described in U.S. Pat. Nos. 4,226,848; 4,292,299; and 4,250,163, and are single layer or bilayer devices having an average thickness of 0.2 to 2.5 mm. The bioadhesive tablets described in these patents utilize a non-adhesive component such as cellulose ether, a bioadhesive component such as polyacrylic acid, sodium carboxymethyl cellulose, or polyvinylpyrrolidone, and a binder for tableting purposes. The cellulose derivatives may or may not be water-soluble. The claimed cellulosic materials in the '299 Patent are methyl cellulose, hydroxypropyl cellulose, and hydroxypropylmethyl cellulose.

The use of bandages or bioadhesive laminated films, which are thin and flexible and therefore have a decreased foreign body sensation, is described in U.S. Pat. Nos. 3,996,934 and 4,286,592. These products are used to deliver drugs through the skin or mucous. The laminated films usually include an adhesive layer, a reservoir layer, and a backing layer. Bioadhesive devices designed to release drug through the skin at a given rate and over a period of time are usually not water soluble, and are not dissolved or washed away by bodily fluids.

In addition to film systems for the delivery of drug through the skin, film delivery systems for use on mucosal surfaces are also known. These types of systems, which are water-insoluble and usually in the form of laminated, extruded or composite films, are described in U.S. Pat. Nos. 4,517,173; 4,572,832; 4,713,243; 4,900,554; and 5,137,729. The '173 Patent describes and claims a membrane-adhering film consisting of at least three layers, including a pharmaceutical layer, a poor water soluble layer, and an intermediate layer. The pharmaceutical layer includes the drug and a cellulose derivative selected from hydroxypropyl cellulose, methyl cellulose, and hydroxypropyl methyl cellulose. The poor water soluble layer is made by the combination of one or more cellulose derivatives with a poor water soluble fatty acid, and the intermediate layer is made of cellulose derivatives. The '832 Patent relates to a soft gelatin film for buccal delivery, made by the combined use of a water soluble protein, a fatty acid ester or carboxyvinyl polymer, and a polyhydric alcohol such as cellulose and polysaccharides, and also teaches the use of coloring or flavoring agents. The '243 Patent describes a single or multi-layered bioadhesive thin film made from 40-95% water soluble hydroxypropyl cellulose, 5-60% water-insoluble ethylene oxide, 0-10% water-insoluble ethyl cellulose, propyl cellulose, polyethylene, or polypropylene, and a medicament. The films are three-layered laminates and include a bioadhesive layer, a reservoir layer, and a non water-soluble outer protective layer. The '729 Patent teaches a soft adhesive film applicable to the oral mucosa containing a systemic drug and comprising a mixture of a vinyl acetate non water-soluble homopolymer, an acrylic acid polymer, and a cellulose derivative. Finally, the '554 Patent describes a device for use in the oral cavity having an adhesive layer including a mixture of an acrylic acid polymer, a water-insoluble cellulose derivative, a pharmaceutical preparation, and a water-insoluble or sparingly soluble backing layer. The adhesive layer contains the pharmaceutical, and upon application to the mucosal surface, delivers the drug. The '554 Patent also states that "it is impossible to achieve an adhesive device for application to body tissue without all three components, that is, acrylic acid polymer, water insoluble cellulose derivative and a water insoluble or sparingly soluble backing layer."

SUMMARY OF THE INVENTION

The present invention is generally a mucoadhesive drug delivery device, comprising one or more biocompatible purified proteins, combined with one or more pharmacologically active agents, one or more mucoadhesive agents and one or more biocompatible solvents. The mucoadhesive devices may further include other additives, such as drug release/diffusion controlling agents and/or optional mucous tissue penetration enhancers.

In one embodiment of the present invention it has been found that mucoadhesive devices including ovalbumin have produced excellent mucoadhesive results. Such embodiment generally comprise ovalbumin combined with one or more mucoadhesive agents (e.g. glycerol), one or more pharmacologically active agents and water. These embodiments have been shown to provide excellent adhesion (e.g. strength and contact duration) and have provided excellent transmucosal delivery of the pharmacologically active agents.

The mucoadhesive delivery systems of the present invention are intended to incorporate drugs that may be delivered locally or systemically. For example, in one embodiment of the present invention a mucoadhesive device may deliver an anesthetic and/or analgesic agent to alleviate the pain associated with many oral mucosal wounds or lesions. The dynamic nature of oral mucosal and its wide range of variable health and tissue characteristics make this a challenging endeavor for the medical and dental community.

The mucoadhesive devices of the present invention provide a new drug delivery biomaterial that is formulated into a mucoadhesive, protein engineered device for transmucosal drug applications. The mucoadhesive devices of the present invention including drugs such as demopressin have been found to provide a controlled systemic release through the oral mucosa. Furthermore, it has been determined that the delivery of pain relief medicaments, such as capsaicin, may be locally administered to the mucosal tissue to alleviate pain caused by wounds and/or lesions.

The mucosa is characterized by an outermost layer of stratified squamous epithelium. Below this layer lies a basement membrane (lamina propria) followed by the submucosa as the innermost layer. The oral epithelium is similar to stratified squamous epithelia found in the rest of the body (e.g., skin) in that it has a mitotically active basal cell layer, advancing through a number of differentiating intermediate layers to the superficial layers, where cells are shed from the surface of the epithelium. The epithelium of the buccal mucosa is about 40-50 cell layers thick, while that of the sublingual mucosa is somewhat thinner. The turnover rate for the buccal epithelium is estimated to be at 5-6 days, which is representative of the entire oral mucosa. The mucosae of tissues subject to mechanical stress, that is the gingiva and hard palate, are keratinized. The mucosa of the soft palate, the sublingual, and the buccal regions are not keratinized. The keratinized epithelia contain neutral lipids like ceramides and acylceramides that serve as a physical barrier, to make the tissue impermeable to water and microorganisms. In contrast, the non-keratinized epithelia, such as the floor of the mouth and the buccal epithelia, do not contain acylceramides and only trace amounts of ceramide. The non-keratinized epithelia have been found to be considerably more permeable to water than keratinized epithelia, thereby enhancing drug absorption.

The oral mucosa in general is somewhat leaky. It is estimated that the water permeability of the oral mucosa is 4-4000 times greater than that of the skin. This wide range in permeability is due to the relative thickness and degree of keratinization of the mucosal tissues. Among the intra-oral sites, the sublingual mucosa (i.e., the tissues lining the inner cheek) are intermediate in permeability. Although there are many factors that affect permeability of drugs through these barriers, including basement membrane, the outer epithelium is considered to be the primary barrier to mucosal penetration.

The cells of oral epithelia are surrounded by mucus, which is comprised mainly of proteins and carbohydrates. This mucus matrix may play a role in cell-cell adhesion, and acts as a barrier and as a lubricant to allow cells to move relative to one another. The mucus matrix may also assist in the bioadhesion of mucoadhesive drug delivery systems. At physiologic pH the mucus network carries a negative charge, due to sialic acid and sulfate residues, and forms a strongly cohesive gel structure that binds to the epithelial cell surface. The mucus comes from the salivary glands and is secreted as part of the saliva. This water rich environment is the chief reason that hydrophilic polymeric matrices are suitable as vehicles for oral the transmucosal mucoadhesive systems of the present invention. The transmucosal mucoadhesive device of the present invention is generally hydrophilic and will breakdown in water when warmed by contact with the mouth in a customized time frame.

Additionally, in some embodiments of the present invention, local and systemic drug delivery through the mucosal tissue has a number of potential applications, including the treatment of bacterial, viral and fungal infections, pain and inflammation, apthous stomatitis, toothaches, periodontal disease and pain/inflammation caused by dental procedures. In one example, the buccal mucosa has an expanse of smooth muscle and its mucosa is relatively immobile compared to sublingual space. Therefore, it can be used to retain transmucosal drug delivery systems. Alternatively, the sublingual area and roof of the mouth are also considered suitable tissue areas for attachment of the mucadhesive devices of the present invention. However, it is again noted that the delivery devices of the present invention are suitable for administration to any of the mucosal tissues of the body.

BRIEF DESCRIPTION OF THE FIGURES

The above mentioned and other advantages of the present invention, and the manner of attaining them, will become more apparent and the invention itself will be better understood by reference to the following description of the embodiments of the invention taken in conjunction with the accompanying drawing, wherein.

DETAILED DESCRIPTION OF THE INVENTION

Figure 1:
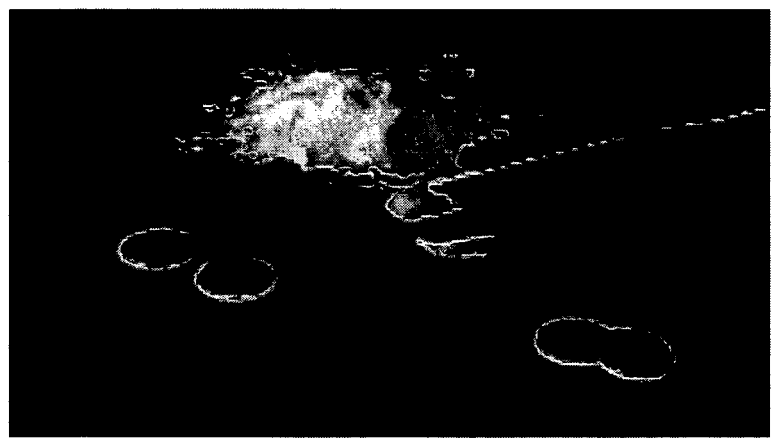
FIG. 1 depicts embodiments of mucoadhesive drug delivery devices of the present invention in wafer and particulate form.

Many embodiments of the mucoadhesive drug delivery devices of the present invention possess some general physiochemical features such as predominantly anionic hydrophilicity with numerous hydrogen bond-forming groups, suitable surface property for wetting mucus/mucosal tissue surfaces and sufficient flexibility to penetrate the mucus network or tissue crevices. Based on the previously mentioned mucoadhesion theories, it may be concluded that the most efficient mucoadhesive drug delivery devices have physicochemical properties that are closely related to those of the mucus substrate. Therefore, the utilization of mucoadhesive proteins, biocompatible solvents and mucoadhesive agents as found in the devices of the present invention provide optimum properties that closely mimic the mucus substrate.

The mucoadhesive devices generally include one or more purified mucoadhesive biocompatible proteins combined with one or more biocompatible solvents, and one or more mucoadhesive agents. In various embodiments of the present invention the mucoadhesive drug delivery devices also include one or more pharmacologically active agents. It is noted that additional additive materials, such as biocompatible polymers like polyanhydride, polylactic acid, polyurethane and the like, and/or other therapeutic entities may be included in the mucoadhesive devices to provide various beneficial features such as noninvasive characteristics, drug release control, patient compliance, ease of use and/or enhanced biocompatibility and drug bioavailability. Generally, the mucoadhesive devices of the present invention include a homogenous distribution of the protein, solvent, mucoadhesive agents and other additives, as well as the homogenous distribution of the pharmacologically active agents.

The purified mucoadhesive proteins may be natural proteins or they may be synthetic or genetically engineered or any combination thereof. In many embodiments of the present invention, the devices include water-absorbing, mucoadhesive proteins. Such water absorbing proteins have an additional affinity to adhere to mucosal tissue thereby providing sufficient time to deliver any pharmacologically active agent included in the device. This differs from other protein devices, such as gelatins, since gelatins require a substantial amount of water, thereby making them more lubricious and reducing their mucoadhesive potential.

Additionally, the proteins of the present invention are generally purified and in a free-form state. Normally, free-form proteins are comprised of protein molecules that are not substantially crosslinked to other protein molecules, unlike tissues or gelatins. Normally, tissue or gelatin is already in a crosslinked matrix form and is thereby limited in forming new intermolecular or intramolecular bonds. Therefore, the purified free-form protein molecules when added to solvent have the capacity to freely associate or intermingle with each other and other molecules or particles, such as solvents, mucoadhesive agents or pharmacologically active agents to form a homogeneous structure. Therefore, the resulting mucoadhesive devices of the present invention include a homogenous distribution of the purified proteins, pharmacologically active agents, mucoadhesive agents, biocompatible solvents and other ingredients. Generally, a homogeneous distribution pertains to the uniform stochiometric intermingling of all types of molecules making up the matrix of the mucoadhesive devices. Additionally, the binding sites of the purified free-form proteins for the attraction and retention of solvent, drug, protein or other molecules are generally available for binding whereas proteins derived from tissues and gelatins have generally lost some or most of their binding capability.

As previously suggested, the mucoadhesive protein utilized may either be naturally occurring, synthetic or genetically engineered and in various embodiments of the present invention are soluble in an aqueous environment. A preferred embodiment of the present invention includes soluble naturally occurring purified protein. Examples of mucoadhesive proteins that may be used in the mucoadhesive drug delivery devices of the present invention include, but are not limited to proteins derived from animal (e.g. mammal, fish, birds . . . ) tissues such as elastin and collagen, or fluids such as serum albumin, fibrinogen and thrombin; animal byproduct proteins, such as egg white proteins (e.g. ovalbumin, plakalbumin . . . ), milk proteins (e.g. casein, lactalbumin, lactoglobulin . . . ); prealbumin, glutamine oligopeptide, keratin, fibronectin, silk, silk fibroin, actin, myosin, fibrinogen, thrombin, aprotinin, antithrombin III and any other biocompatible natural protein. Additionally, plant proteins, such as whey protein (e.g. betalactoglobulin and alphlactalbumin), rice protein, grape vine protein, grape leaf protein, maize protein, olive protein, canola protein, soy protein, cottonseed protein, cotton leaf protein, seaweed protein, wheat protein (e.g. agglutinen) tobacco proteins (e.g. tobacco leaf, root and stem proteins such as F1 and F2 protein), and chickpea protein.

Preferred mucoadhesive proteins found to have enhanced mucoadhesive properties when included in the mucoadhesive devices of the present invention are egg white proteins such as ovalbumin, and plant proteins such as soy proteins, whey protein (e.g. betalactoglobulin and alphlactalbumin), rice protein, grape vine protein, grape leaf protein, maize protein, olive protein, canola protein, cottonseed protein, cotton leaf protein, seaweed protein, wheat protein such as agglutinin, tobacco proteins (leaf, root, stem) such as F1 and F2 protein, chickpea protein and fish protein. One type of protein that has produced exemplary results in embodiments of the present invention has been egg albumen (e.g. ovalbumin). Examples of other proteins that are commercially available and may be utilized in some embodiments of the present invention include Type I soluble collagen, soluble elastin, and soluble albumin manufactured by Kensey Nash Corporation, 55 East Uwchlan Avenue, Exton, Pa. 19341, Sigma-Aldrich Corporation, St. Louis, Mo., USA or Elastin Products Company, Inc., P.O. Box 568, Owensville, Mo., USA 65066. It is noted that combinations of natural proteins may be utilized to optimize desirable characteristics of the resulting mucoadhesive delivery devices, such as mucoadhesive enhancement, strength, degradability, drug resorption, etc.

As previously suggested the proteins of the present invention are generally purified proteins. The purity of each natural protein component mixed in the coatable composition phase (the coatable composition will be described further below) during production of particles include 20% or less other proteins or impurities, preferably 10% or less other proteins or impurities, more preferably 3% or less other proteins or impurities and if available ideally 1% or less other proteins or impurities.

Other proteins that may be utilized in the mucoadhesive devices of the present invention, such as synthetic proteins, are generally prepared by chemical synthesis utilizing techniques known in the art. Also, individual proteins may be chemically combined with one or more other proteins of the same or different type to produce a dimer, trimer or other multimer or fragmented to produce protein fragments or parts. A simple advantage of having a larger protein molecule is that it will make interconnections with other protein molecules to create a stronger delivery device that is less susceptible to dissolving when implanted, injected, attached or administered upon the mucous membrane and provides additional protein structural and biochemical characteristics.

Additional, protein molecules can also be chemically combined to any other chemical so that the chemical does not release from the mucoadhesive proteins. In this way, the chemical entity can provide surface modifications to the mucoadhesive device or structural contributions to the device to produce specific characteristics. The surface modifications can enhance and/or facilitate mucosal attachment depending on the chemical substance. The structural modifications can be used to facilitate or impede dissolution, enzymatic degradation or dissolution of the mucoadhesive delivery device.

Synthetic mucoadhesive proteins may be cross-linked, linked, bonded, chemically and/or physically linked to pharmacological active agents, enzymatically, chemically or thermally cleaved and utilized alone or in combination with other proteins partial proteins (e.g. peptides), lipids, carbohydrates and/or drugs, to form the mucoadhesive proteins. Examples of such synthetic mucoadhesive proteins include, but are not limited to heparin-protein, chondroitin-protein, GAGs-collagen, heparin-collagen, collagen-elastin-heparin, collagen-albumin, collagen-albumin-heparin, albumin-polyethylene glycol, collagen-albumin-elastin-heparin, collagen-hyaluronic acid, collagen-chondroitin-heparin, collagen-chondroitin, albumin-lethecin, albumin-cellulose, albumin-casein, albumin-soy protein, albumin-wheat protein, albumin-retinol and the like.

Finally, genetically engineered proteins may be utilized in the mucoadhesive devices of the present invention. A specific example of a particularly preferred genetically engineered protein for use in the devices of the present invention is human collagen produced by FibroGen, Inc., 225 Gateway Blvd., South San Francisco, Calif. 94080. Other examples of particularly preferred genetically engineered proteins for use in the mucoadhesive devices of the present invention are commercially available under the nomenclature "ELP", "SLP", "CLP", "SLPL", "SLPF" and "SELP" from Protein Polymer Technologies, Inc. San Diego, Calif. ELP's, SLP's, CLP's, SLPL's, SLPF's and SELP's are families of genetically engineered protein polymers consisting of silklike blocks, elastinlike blocks, collagenlike blocks, lamininlike blocks, fibronectinlike blocks and the combination of silklike and elastinlike blocks, respectively. The ELP's, SLP's, CLP's, SLPL's, SLPF's and SELP's are produced in various block lengths and compositional ratios. Generally, blocks include groups of repeating amino acids making up a peptide sequence that occurs in a protein. Genetically engineered proteins are qualitatively distinguished from sequential polypeptides found in nature in that the length of their block repeats can be greater (up to several hundred amino acids versus less than ten for sequential polypeptides) and the sequence of their block repeats can be almost infinitely complex. Table A depicts examples of genetically engineered blocks. Table A and a further description of genetically engineered blocks may be found in Franco A. Ferrari and Joseph Cappello, *Biosynthesis of Protein Polymers*, in: Protein-Based Materials, (eds., Kevin McGrath and David Kaplan), Chapter 2, pp. 37-60, Birkhauser, Boston (1997).

TABLE A

Protein polymer sequences

| Polymer Name | Monomer Amino Acid Sequence |
|---|---|
| SLP 3 | $[(GAGAGS)_9 \, GAAGY)]$ |
| SLP 4 | $(GAGAGS)_n$ |
| SLP F | $[(GAGAGS)_9 \, GAA \, VTGRGDSPAS \, AAGY]_n$ |
| SLP L3.0 | $[(GAGAGS)_9 \, GAA \, PGASIKVAVSAGPS \, AGY]_n$ |
| SLP L3.1 | $[(GAGAGS)_9 \, GAA \, PGASIKVAVSGPS \, AGY]_n$ |
| SLP F9 | $[(GAGAGS)_9 \, RYVVLPRPVCFEK \, AAGY]_n$ |
| ELP I | $[(VPGVG)_4]_n$ |
| SELP 0 | $[(GVGVP)_8 \, (GAGAGS)_2]_n$ |
| SELP 1 | $[GAA \, (VPGVG)_4 \, VAAGY \, (GAGAGS)_9]_n$ |
| SELP 2 | $[(GAGAGS)_6 \, GAAGY \, (GAGAGS)_5 \, (GVGVP)_8]_n$ |
| SELP 3 | $[(GVGVP)_8 \, (GAGAGS)_8]_n$ |
| SELP 4 | $[(GVGVP)_{12} \, (GAGAGS)_8]_n$ |
| SELP 5 | $[(GVGVP)_{16} \, (GAGAGS)_8]_n$ |
| SELP 6 | $[(GVGVP)_{32} \, (GAGAGS)_8]_n$ |
| SELP 7 | $[(GVGVP)_8 \, (GAGAGS)_6]_n$ |
| SELP 8 | $[(GVGVP)_8 \, (GAGAGS)_4]_n$ |
| KLP 1.2 | $[(AKLKLAEAKLELAE)_4]_n$ |
| CLP 1 | $[GAP(GPP)_4]_n$ |
| CLP 2 | $\{[GAP(GPP)_4]_2 \, GPAGPVGSP\}_n$ |

TABLE A-continued

Protein polymer sequences

| Polymer Name | Monomer Amino Acid Sequence |
|---|---|
| CLP-CB | {[GAP(GPP)₄]₂ (GLPGPKGDRGDAGPKGADGSPGPA) GPAGPVGSP}ₙ |
| CLP 3 | (GAPGAPGSQGAPGLQ)ₙ |

Repetitive amino acid sequences of selected protein polymers.
SLP = silk like protein;
SLPF = SLP containing the RGD sequence from fibronectin;
SLPL 3/0 and SLPL 3/1 = SLP containing two difference sequences from laminin protein;
ELP = elastin like protein;
SELP = silk elastin like protein;
CLP = collagen like protein;
CLP-CB = CLP containing a cell binding domain from human collagen;
KLP = keratin like protein The nature of the elastinlike blocks, and their length and position within the monomers influences the water solubility of the SELP polymers. For example, decreasing the length and/or content of the silklike block domains, while maintaining the length of the elastinlike block domains, increases the water solubility of the polymers. For a more detailed discussion of the production of SLP's, ELP's, CLP's, SLPF's and SELP's as well as their properties and characteristics see, for example, in J. Cappello et al., *Biotechnol. Prog.*, 6, 198 (1990), the full disclosure of which is incorporated by reference herein. One preferred SELP, SELP7, has an elastin:silk ratio of 1.33, and has 45% silklike protein material and is believed to have weight average molecular weight of 80,338.

Generally, the amount of purified protein found in embodiments of the mucoadhesive devices of the present invention may vary between from about 15% to about 85%, preferably from about 20% to 80% by weight, and most preferably from about 50% to 70% by weight based upon the weight of the final particles. As used herein, unless stated otherwise, all percentages are percentages based upon the total mass of the composition or devices being described, e.g., 100% is total.

The mucoadhesive delivery devices utilized in various embodiments of the present invention also include one or more biocompatible solvents. By using a biocompatible solvent, the risk of adverse tissue reactions to the solvent is minimized. Additionally, the use of a biocompatible solvent reduces the potential structural and/or pharmacological degradation of the pharmacologically active agent that some such pharmacologically active agents undergo when exposed to organic solvents. Suitable biocompatible solvents for use in the method of the present invention include, but are not limited to, water; saline; dimethyl sulfoxide (DMSO); biocompatible alcohols, such as methanol and ethanol; various acids, such as formic acid; oils, such as olive oil, peanut oil and the like; and combinations of these and the like. Preferably, the biocompatible solvent comprises water. Generally, the amount of biocompatible solvent suitable to wet and or dissolve the protein components for use in the method of the present invention will range from about 50% to about 10000%, preferably from about 100% to about 5000% and more preferably from about 200% to about 1000% by weight, based upon the weight and/or amount of the protein.

As used herein, unless stated otherwise, all percentages are percentages based upon the weight of the identified final form.

Additionally, a mucoadhesive agent, such as humectants, may be utilized in the devices of the present invention to make the matrix more water absorbing thereby enhancing mucoadhesion. Generally, the mucoadhesive agents possess humectant properties being that they are substances that promote the retention of moisture. Examples of mucoadhesive agents include but are not limited to glycerin, pectin, polyethylene glycol, sorbitol, maltitol, mannitol, hydrogenated glucose syrups, xylitol, polydextrose, glyceryl triacetate, propylene glycol, propylene glycol alginate, sodium alginate, castor oil and some polysaccharides such as glycogen. Generally, the amount of mucoadhesive agents used in the method of the present invention will range from about 0.1% to about 35%, preferably from about 5% to about 30% and more preferably from about 10% to about 25% by weight, based upon the weight of the mucoadhesive device.

In addition, the mucoadhesive drug delivery devices of the present invention may include one or more pharmacologically active agents. As used herein, "pharmacologically active agent" generally refers to a pharmacologically active agent having a direct or indirect beneficial therapeutic effect upon introduction into a host. Pharmacologically active agents further includes neutraceuticals. The phrase "pharmacologically active agent" is also meant to indicate prodrug forms thereof. A "prodrug form" of a pharmacologically active agent means a structurally related compound or derivative of the pharmacologically active agent which, when administered to a host is converted into the desired pharmacologically active agent. A prodrug form may have little or none of the desired pharmacological activity exhibited by the pharmacologically active agent to which it is converted. Representative examples of pharmacologically active agents that may be suitable for use in the mucoadhesive devices of the present invention include, but are not limited to, (grouped by therapeutic class):

Antidiarrheals such as diphenoxylate, loperamide and hyoscyamine;

Antihypertensives such as hydralazine, minoxidil, captopril, enalapril, clonidine, prazosin, debrisoquine, diazoxide, guanethidine, methyldopa, reserpine, trimethaphan;

Calcium channel blockers such as diltiazem, felodipine, amlodipine, nitrendipine, nifedipine and verapamil;

Antiarrhythmics such as amiodarone, flecainide, disopyramide, procainamide, mexiletene and quinidine, Antiangina agents such as glyceryl trinitrate, erythrityl tetranitrate, pentaerythritol tetranitrate, mannitol hexanitrate, perhexilene, isosorbide dinitrate and nicorandil;

Beta-adrenergic blocking agents such as alprenolol, atenolol, bupranolol, carteolol, labetalol, metoprolol, nadolol, nadoxolol, oxprenolol, pindolol, propranolol, sotalol, timolol and timolol maleate;

Cardiotonic glycosides such as digoxin and other cardiac glycosides and theophylline derivatives;

Adrenergic stimulants such as adrenaline, ephedrine, fenoterol, isoprenaline, orciprenaline, rimeterol, salbutamol, salmeterol, terbutaline, dobutamine, phenylephrine, phenylpropanolamine, pseudoephedrine and dopamine;

Vasodilators such as cyclandelate, isoxsuprine, papaverine, dipyrimadole, isosorbide dinitrate, phentolamine, nicotinyl alcohol, co-dergocrine, nicotinic acid, glycerl trinitrate, pentaerythritol tetranitrate and xanthinol;

Antiproliferative agents such as paclitaxel, estradiol, actinomycin D, sirolimus, tacrolimus, everolimus and dexamethasone;

Antimigraine preparations such as ergotanmine, dihydroergotamine, methysergide, pizotifen and sumatriptan;

Anticoagulants and thrombolytic agents such as warfarin, dicoumarol, low molecular weight heparins such as enoxaparin, streptokinase and its active derivatives;

Hemostatic agents such as aprotinin, tranexamic acid and protamine;

Analgesics and antipyretics including the opioid analgesics such as buprenorphine, dextromoramide, dextropropoxyphene, fentanyl, alfentanil, sufentanil, hydromorphone, methadone, morphine, oxycodone, papaveretum, pentazocine, pethidine, phenopefidine, codeine dihydrocodeine; acetylsalicylic acid (aspirin), paracetamol, and phenazone;

Immunosuppressants, antiproliferatives and cytostatic agents such as rapamycin (sirolimus) and its analogs (everolimus and tacrolimus);

Neurotoxins such as capsaicin, botulinum toxin (botox);

Hypnotics and sedatives such as the barbiturates amylobarbitone, butobarbitone and pentobarbitone and other hypnotics and sedatives such as chloral hydrate, chlormethiazole, hydroxyzine and meprobamate;

Antianxiety agents such as the benzodiazepines alprazolam, bromazepam, chlordiazepoxide, clobazam, chlorazepate, diazepam, flunitrazepam, flurazepam, lorazepam, nitrazepam, oxazepam, temazepam and triazolam;

Neuroleptic and antipsychotic drugs such as the phenothiazines, chlorpromazine, fluphenazine, pericyazine, perphenazine, promazine, thiopropazate, thioridazine, trifluoperazine; and butyrophenone, droperidol and haloperidol; and other antipsychotic drugs such as pimozide, thiothixene and lithium;

Antidepressants such as the tricyclic antidepressants amitryptyline, clomipramine, desipramine, dothiepin, doxepin, imipramine, nortriptyline, opipramol, protriptyline and trimipramine and the tetracyclic antidepressants such as mianserin and the monoamine oxidase inhibitors such as isocarboxazid, phenelizine, tranylcypromine and moclobemide and selective serotonin re-uptake inhibitors such as fluoxetine, paroxetine, citalopram, fluvoxamine and sertraline;

CNS stimulants such as caffeine and 3-(2-aminobutyl) indole;

Anti-alzheimer's agents such as tacrine;

Anti-Parkinson's agents such as amantadine, benserazide, carbidopa, levodopa, benztropine, biperiden, benzhexol, procyclidine and dopamine-2 agonists such as S (−)-2-(N-propyl-N-2-thienylethylamino)-5-hydroxytetralin (N-0923), Anticonvulsants such as phenytoin, valproic acid, primidone, phenobarbitone, methylphenobarbitone and carbamazepine, ethosuximide, methsuximide, phensuximide, sulthiame and clonazepam, Antiemetics and antinauseants such as the phenothiazines prochloperazine, thiethylperazine and 5HT-3 receptor antagonists such as ondansetron and granisetron, as well as dimenhydrinate, diphenhydramine, metoclopramide, domperidone, hyoscine, hyoscine hydrobromide, hyoscine hydrochloride, clebopride and brompride;

Non-steroidal anti-inflammatory agents including their racemic mixtures or individual enantiomers where applicable, preferably which can be formulated in combination with dermal and/or mucosal penetration enhancers, such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketorolac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate;

Antirheumatoid agents such as penicillamine, aurothioglucose, sodium aurothiomalate, methotrexate and auranofin;

Muscle relaxants such as baclofen, diazepam, cyclobenzaprine hydrochloride, dantrolene, methocarbamol, orphenadrine and quinine;

Agents used in gout and hyperuricaemia such as allopurinol, colchicine, probenecid and sulphinpyrazone;

Oestrogens such as oestradiol, oestriol, oestrone, ethinyloestradiol, mestranol, stilboestrol, dienoestrol, epioestriol, estropipate and zeranol;

Progesterone and other progestagens such as allyloestrenol, dydrgesterone, lynoestrenol, norgestrel, norethyndrel, norethisterone, norethisterone acetate, gestodene, levonorgestrel, medroxyprogesterone and megestrol;

Antiandrogens such as cyproterone acetate and danazol;

Antioestrogens such as tamoxifen and epitiostanol and the aromatase inhibitors, exemestane and 4-hydroxy-androstenedione and its derivatives;

Androgens and anabolic agents such as testosterone, methyltestosterone, clostebol acetate, drostanolone, furazabol, nandrolone oxandrolone, stanozolol, trenbolone acetate, dihydro-testosterone, 17-(α-methyl-19-noriestosterone and fluoxymesterone;

5-alpha reductase inhibitors such as finasteride, turosteride, LY-191704 and MK-306;

Corticosteroids such as betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate, methylprednisolone, prednisolone, prednisolone 21-phosphate, prednisone, triamcinolone, triamcinolone acetonide;

Glycosylated proteins, proteoglycans, glycosaminoglycans such as chondroitin sulfate; chitin, acetyl-glucosamine, hyaluronic acid;

Complex carbohydrates such as glucans;

Further examples of steroidal anti-inflammatory agents such as cortodoxone, fludroracetonide, fludrocortisone, difluorsone diacetate, flurandrenolone acetonide, medrysone, amcinafel, amcinafide, betamethasone and its other esters, chloroprednisone, clorcortelone, descinolone, desonide, dichlorisone, difluprednate, flucloronide, flumethasone, flunisolide, flucortolone, fluoromethalone, fluperolone, fluprednisolone, meprednisone, methylmeprednisolone, paramethasone, cortisone acetate, hydrocortisone cyclopentylpropionate, cortodoxone, flucetonide, fludrocortisone acetate, flurandrenolone, aincinafal, amcinafide, betamethasone, betamethasone benzoate, chloroprednisone acetate, clocortolone acetate, descinolone acetonide, desoximetasone, dichlorisone acetate, difluprednate, flucloronide, flumethasone pivalate, flunisolide acetate, fluperolone acetate, fluprednisolone valerate, paramethasone acetate, prednisolamate, prednival, triamcinolone hexacetonide, cortivazol, formocortal and nivazol;

Pituitary hormones and their active derivatives or analogs such as corticotrophin, thyrotropin, follicle stimulating hormone (FSH), luteinising hormone (LH) and gonadotrophin releasing hormone (GnRH);

Hypoglycemic agents such as insulin, chlorpropamide, glibenclamide, gliclazide, glipizide, tolazamide, tolbutamide and metformin;

Thyroid hormones such as calcitonin, thyroxine and liothyronine and antithyroid agents such as carbimazole and propylthiouracil;

Other miscellaneous hormone agents such as octreotide;

Pituitary inhibitors such as bromocriptine;

Ovulation inducers such as clomiphene;

Diuretics such as the thiazides, related diuretics and loop diuretics, bendrofluazide, chlorothiazide, chlorthalidone, dopamine, cyclopenthiazide, hydrochlorothiazide, indapamide, mefruside, methycholthiazide, metolazone, quinethazone, bumetanide, ethacrynic acid and frusemide and potassium sparing diuretics, spironolactone, amiloride and triamterene;

Antidiuretics such as desmopressin, lypressin and vasopressin including their active derivatives or analogs;

Obstetric drugs including agents acting on the uterus such as ergometrine, oxytocin and gemeprost;

Prostaglandins such as alprostadil (PGE1), prostacyclin (PGI2), dinoprost (prostaglandin F2-alpha) and misoprostol;

Antimicrobials including the cephalosporins such as cephalexin, cefoxytin and cephalothin;

Penicillins such as amoxycillin, amoxycillin with clavulanic acid, ampicillin, bacampicillin, benzathine penicillin, benzylpenicillin, carbenicillin, cloxacillin, methicillin, phenethicillin, phenoxymethylpenicillin, flucloxacillin, meziocillin, piperacillin, ticarcillin and azlocillin;

Tetracyclines such as minocycline, chlortetracycline, tetracycline, demeclocycline, doxycycline, methacycline and oxytetracycline and other tetracycline-type antibiotics;

Amnioglycoides such as amikacin, gentamicin, kanamycin, neomycin, netilmicin and tobramycin;

Antifungals such as amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione;

Quinolones such as nalidixic acid, cinoxacin, ciprofloxacin, enoxacin and norfloxacin;

Sulphonamides such as phthalysulphthiazole, sulfadoxine, sulphadiazine, sulphamethizole and sulphamethoxazole;

Sulphones such as dapsone;

Other miscellaneous antibiotics such as chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonarn, colistin IV, metronidazole, tinidazole, fusidic acid, trimethoprim, and 2-thiopyridine N-oxide; halogen compounds, particularly iodine and iodine compounds such as iodine-PVP complex and diiodohydroxyquin, hexachlorophene; chlorhexidine; chloroamine compounds; and benzoylperoxide;

Antituberculosis drugs such as ethambutol, isoniazid, pyrazinamide, rifampicin and clofazimine;

Antimalarials such as primaquine, pyrimethamine, chloroquine, hydroxychloroquine, quinine, mefloquine and halofantrine;

Antiviral agents such as acyclovir and acyclovir prodrugs, famcyclovir, zidovudine, didanosine, stavudine, lamivudine, zalcitabine, saquinavir, indinavir, ritonavir, n-docosanol, tromantadine and idoxuridine;

Anthelmintics such as mebendazole, thiabendazole, niclosamide, praziquantel, pyrantel embonate and diethylcarbamazine;

Cytotoxic agents such as plicamycin, cyclophosphamide, dacarbazine, fluorouracil and its prodrugs (described, for example, in *International Journal of Pharmaceutics*, 111, 223-233 (1994)), methotrexate, procarbazine, 6-mercaptopurine and mucophenolic acid;

Anorectic and weight reducing agents including dexfenflurarnine, fenfluramine, diethylpropion, mazindol and phentermine;

Agents used in hypercalcaemia such as calcitriol, dihydrotachysterol and their active derivatives or analogs;

Antitussives such as ethylmorphine, dextromethorphan and pholcodine;

Expectorants such as carbolcysteine, bromihexine, emetine, quanifesin, ipecacuanha and saponins;

Decongestants such as phenylephrine, phenylpropanolamine and pseudoephedrine;

Bronchospasm relaxants such as ephedrine, fenoterol, orciprenaline, rimiterol, salbutamol, sodium cromoglycate, cromoglycic acid and its prodrugs (described, for example, in *International Journal of Pharmaceutics* 7, 63-75 (1980)), terbutaline, ipratropium bromide, salmeterol and theophylline and theophylline derivatives;

Antihistamines such as meclozine, cyclizine, chlorcyclizine, hydroxyzine, brompheniramine, chlorpheniramine, clemastine, cyproheptadine, dexchlorpheniramine, diphenhydramine, diphenylamine, doxylamine, mebhydrolin, pheniramine, tripolidine, azatadine, diphenylpyraline, methdilazine, terfenadine, astemizole, loratidine and cetirizine;

Local anaesthetics such as benzocaine, bupivacaine, amethocaine, lignocaine, lidocaine, cocaine, cinchocaine, dibucaine, mepivacaine, prilocaine, etidocaine, veratridine (specific c-fiber blocker) and procaine;

Stratum corneum lipids, such as ceramides, cholesterol and free fatty acids, for improved skin barrier repair [Man, et al. *J. Invest. Dermatol.*, 106(5), 1096, (1996)];

Neuromuscular blocking agents such as suxamethonium, alcuronium, pancuronium, atracurium, gallamine, tubocurarine and vecuronium;

Smoking cessation agents such as nicotine, bupropion and ibogaine;

Insecticides and other pesticides which are suitable for local application;

Dermatological agents, such as vitamins A, C, B1, B2, B6, B 12, B 12α., and E, vitamin E acetate and vitamin E sorbate;

Allergens for desensitisation such as house, dust or mite allergens;

Nutritional agents and neutraceuticals, such as vitamins, essential amino acids and fats;

Macromolecular pharmacologically active agents such as proteins, enzymes, peptides, polysaccharides (such as cellulose, amylose, dextran, chitin), nucleic acids, cells, tissues, and the like;

Bone mending biochemicals such as calcium carbonate, calcium phosphate, hydroxyapetite or bone morphogenic protein (BMP);

Angiogenic growth factors such as Vascular Endothelial Growth Factor (VEGF) and epidermal growth factor (EFG), cytokines interleukins, fibroblasts and cytotaxic chemicals; and Keratolytics such as the alpha-hydroxy acids, glycolic acid and salicylic acid; and DNA, RNA or other oligonucleotides.

Additionally, the mucoadhesive drug delivery devices of the present invention are particularly advantageous for the encapsulation, incorporation and/or scaffolding of macromolecular pharmacologically active agents such as proteins, enzymes, peptides, polysaccharides, nucleic acids, cells, tissues, and the like. Immobilization of macromolecular pharmacologically active agents into or onto a device can be difficult due to the ease with which some of these macromolecular agents denature when exposed to organic solvents, constituents present in bodily fluids or to temperatures appreciably higher than room temperature. However, since the method of the present invention utilizes biocompatible solvents such as water, saline, DMSO or ethanol the risk of the denaturation of these types of materials is reduced. Furthermore, due to the size of these macromolecular pharmacologically active agents, these agents may be encapsulated within the devices of the present invention and thereby are protected from constituents of bodily fluids that would otherwise denature them. Thus, the devices of the present invention allow these macromolecular agents to exert their therapeutic effects, while yet protecting them from denaturation or other structural degradation.

Examples of proteins and/or polypeptides which can be incorporated into the mucoadhesive devices of the present invention include, but are not limited to, hemoglobin, vasporessin, oxytocin, endorphin, lutein, lutenizing hormone, estrogen, testosterone, adrenocorticocotrophic hormone, epidermal growth factor, prolactin, luliberin or luteinising hormone releasing factor, human growth factor, and the like; enzymes such as adenosine deaminase, superoxide dismutase, xanthine oxidase, and the like; enzyme systems; blood clotting factors; clot inhibitors or clot dissolving agents such as streptokinase and tissue plasminogen activator; antigens for immunization; hormones (e.g. steroid, polypeptide . . . ); polysaccharides such as heparin; oligonucleotides; bacteria and other microbial microorganisms including viruses; monoclonal antibodies, such as herceptin and rituximab; vitamins; cofactors; growth factors; retroviruses for gene therapy, combinations of these and the like.

An efficacious amount of the aforementioned pharmacologically active agent(s) can easily be determined by those of ordinary skill in the art taking into consideration such parameters as the particular pharmacologically active agent chosen, the size and weight of the patient, the desired therapeutic effect, the pharmacokinetics of the chosen pharmacologically active agent, and the like, as well as by reference to well known resources such as Physicians' Desk Reference®: PDR—57 ed (2003)—Medical Economics 1974. In consideration of these parameters, it has been found that a wide range exists in the amount of the pharmacologically active agent(s) capable of being incorporated into and subsequently released from or alternatively allowed to exert the agent's therapeutic effects from within the mucoadhesive drug delivery devices. More specifically, the amount of pharmacologically active agent that may be incorporated into and then either released from or active from within the mucoadhesive devices may range from about 0.00001% to about 95%, more preferably, from about 0.001% to about 80%, most preferably from about 0.1% to 60%, based on the weight of the mucoadhesive devices. It is important to note that the pharmacologically active agents are generally homogenously distributed throughout the mucoadhesive devices thereby allowing for a controlled release of these agents.

Finally, one or more additive materials may be added to the mucoadhesive drug delivery devices to manipulate the material properties and thereby add additional structure or modify the release of pharmacologically active agents. That is, while a mucoadhesive device that includes a relatively fast-degrading protein material without a particular additive material will readily degrade thereby releasing drug relatively quickly upon insertion or implantation, a mucoadhesive device that includes a particular polymeric material, such as polyanhydride, will degrade slowly, as well as release the pharmacologically active agent(s) over a longer period of time. For example, insoluble purified proteins that are commercially available and may be utilized in some embodiments of the present invention include Type I insoluble collagen and insoluble elastin, manufactured by Kensey Nash Corporation, 55 East Uwchlan Avenue, Exton, Pa. 19341, Sigma-Aldrich Corporation, St. Louis, Mo., USA or Elastin Products Company, Inc., P.O. Box 568, Owensville, Mo., USA 65066. Other examples of biodegradable and/or biocompatible additive materials suitable for use in the mucoadhesive drug delivery devices of the present invention include, but are not limited to polyurethanes, vinyl homopolymers and copolymers, acrylate homopolymers and copolymers, polyethers, cellulosics, epoxies, polyesters, acrylics, nylons, silicones, polyanhydride, poly(ethylene terephthalate), polyacetal, poly(ethylene oxide)/poly(butylene terephthalate) copolymer, polycarbonate, poly(tetrafluoroethylene) (PTFE), polycaprolactone, polyethylene oxide, poly(vinyl chloride), polylactic acid, polyglycolic acid, polypropylene oxide, poly(akylene) glycol, polyoxyethylene, sebacic acid, polyvinyl alcohol (PVA), 2-hydroxyethyl methacrylate (HEMA), polymethyl methacrylate, 1,3-bis(carboxyphenoxy)propane, lipids, phosphatidylcholine, triglycerides, polyhydroxybutyrate (PHB), polyhydroxyvalerate (PHV), poly(ethylene oxide) (PEO), poly ortho esters, poly (amino acids), polycynoacrylates, polyphophazenes, polysulfone, polyamine, poly (amido amines), fibrin, graphite, flexible fluoropolymer, isobutyl-based, isopropyl styrene, vinyl pyrrolidone, cellulose acetate dibutyrate, guar gum, xanthan gum, sodium carboxymethyl cellulose, tragacanth gum, silicone rubber, copolymers of these, and the like. Other materials that may be incorporated into the coatable composition to provide enhanced features include, but are not limited to, ceramics, bioceramics, glasses bioglasses, glass-ceramics, resin cement, resin fill; more specifically, glass ionomer, hydroxyapatite, calcium sulfate, $Al_2O_3$, tricalcium phosphate, calcium phosphate salts, sugars, starches, carbohydrates, salts, polysaccharides, and carbon. Additional other materials that may be incorporated into the coatable composition include alloys such as, cobalt-based, galvanic-based, stainless steel-based, titanium-based, zirconium oxide, zirconia, silica, aluminum-based, vanadium-based, molybdenum-based, nickel-based, iron-based, or zinc-based (zinc phosphate, zinc polycarboxylate).

Other additives may be utilized, for example, to facilitate the processing of the mucoadhesive devices, to stabilize the pharmacologically active agents, to facilitate the activity of the pharmacologically active agents, to enhance the permeation of the pharmacologically active agents into the mucosal tissue or to alter the release characteristics of the biocompatible protein particles. For example, when the pharmacologically active agent is to be an enzyme, such as xanthine oxidase or superoxide dismutase, the protein matrix device may further comprise an amount of an enzyme substrate, such as xanthine, to facilitate the action of the enzyme. Another example may be the inclusion of permeation enhancers in the mucoadhesive devices to assist in facilitating the absorption of the pharmacologically active agents into the mucosal tissue. Examples of permeation enhancers (e.g. membrane permeation enhancers) include, but are not limited to, reagents such as ascorbic acid, citric acid, glutamine and Lauroylcarnitine.

Additionally, hydrophobic substances such as lipids can be incorporated into the biocompatible protein particles to extend the duration of drug release, while hydrophilic, polar additives, such as salts and amino acids, can be added to facilitate, i.e., shorten the duration of, drug release. Exemplary hydrophobic substances include lipids, e.g., tristeafin, ethyl stearate, phosphotidycholine, polyethylene glycol (PEG); fatty acids, e.g., sebacic acid erucic acid; combinations of these and the like. A particularly preferred hydrophobic additive useful to extend the release of the pharmacologically active agents comprises a combination of a dimer of erucic acid and sebacic acid, wherein the ratio of the dimer of erucic acid to sebacic acid is 1:4. Exemplary hydrophilic additives useful to shorten the release duration of the pharmacologically active agent include but are not limited to, salts, such as sodium chloride; and amino acids, such as glutamine and glycine. If additives are to be incorporated into the coatable composition, they will preferably be included in an amount so that the desired result of the additive is exhibited.

One method of producing the mucoadhesive devices of the present invention is by providing one or more selected mucoadhesive proteins, adding other materials (pharmacologically active agents, additives, mucoadhesive agents, etc.) and solvents (water) to form a coatable composition. Once prepared, the coatable composition may be coated onto any suitable surface from which it may be released after drying by any suitable method. Examples of suitable coating techniques include spin coating, gravure coating, flow coating, spray coating, coating with a brush or roller, screen printing, knife coating, curtain coating, slide curtain coating, extrusion, squeegee coating, and the like. The coated film (preferably having a substantially planar body having opposed major surfaces) is desirably thin enough so as to be capable of drying within a reasonable amount of time and also thin enough so that the film can be formed into a cohesive body comprising a substantially homogeneous dispersion of the components of the coatable composition. For example, a thinner film will tend to form a more homogeneous cohesive body when the film is formed into the shape of a cylinder. A typical coated film of the coatable composition have a thickness in the range of from about 0.01 millimeters to about 20 millimeters, more preferably from about 0.05 millimeters to about 5 millimeters.

Intially, when the film is first coated, it is likely to be non-cohesive, fluidly-flowable, and/or non self-supporting. Thus, the coated film is preferably dried sufficiently so that it becomes cohesive, i.e., the film preferably sticks to itself rather than other materials. The film may simply be allowed to dry at room temperature, or alternatively, may be dried under vacuum under conditions of mild heating or conditions of mild cooling. Heating the coatable composition is generally not utilized. However, when utilizing heat to dry the film, care should be taken to avoid denaturation or structural degradation of the pharmacologically active agent incorporated therein. Also, care should be taken to not irreversibly denature the proteins of the coatable composition or cohesive body during preparation through various actions on the composition that will disrupt the secondary and/or tertiary structure of the protein(s) such as application of excessive heat or strong alkaline or acid solution, which may cause coagulation/gelation. See table 1 for example of lost mucoadhesive characteristics of heated protein materials. Such coagulation or gelation will excessively inhibit the mucoadhesive function of the device. It is noted that the cohesive body may be prepared without the film step if the proper amounts of protein, solvent and other components are known to achieve the necessary characteristics of the cohesive body.

The specific solvent content at which the film becomes cohesive unto itself will depend on the individual components incorporated into the coatable composition. A cohesive body is achieved when the components of the composition are in the proper amounts so that the resulting composition is tacky or cohesive to itself more than to other materials or surface that it contacts. Generally, films that have too high of a solvent content will not be cohesive. Films that have too low of a solvent content will tend to crack, shatter, or otherwise break apart upon efforts to form them into a cohesive body. With these considerations in mind, the solvent content of a partially dried film will preferably be from about 8% to about 80%, more preferably from about 12% to about 50% and most preferably from about 15% to about 45%.

Additionally, embodiments of the present invention may include the addition of reagents to properly pH the resulting mucoadhesive devices and thereby enhance the biocompatible and/or mucoadhesive characteristics of the device with the host tissue of which it is to be administered. When preparing the coatable composition and/or cohesive body, the pH steps of the mixture of biocompatible materials, such as purified proteins, mucoadesive agents, pharmacologically active agents and other additives, and the biocompatable solvent(s), occur during the preparation of the coatable composition or may occur after the cohesive body is formed. For example, the pH steps can be started with the addition of biocompatable solvent to the protein or to the mixture of protein material and optional biocompatible materials, or the pH steps can be started after mixing the material(s) and solvent(s) together before the cohesive body is formed. In various embodiments of the present invention, the pH steps can include the addition of drops of 0.05N to 4.0N acid or base to the solvent wetted material until the desired pH is reached as indicated by a pH meter, pH paper or any pH indicator. More preferably, the addition of drops of 0.1N-0.5 N acid or base are used. Although any acid or base may be used, the preferable acids and bases are HCl and NaOH, respectively. If known amounts of biocompatible material are used it may be possible to add acid or base to adjust the pH when the biocompatable material is first wetted, thereby allowing wetting and pH adjustments to occur in one step. Alternatively, the pH steps may be performed after the cohesive body is formed by applying the acid or base after the cohesive body is formed.

Furthermore, the cohesive body and/or mucoadhesive device may be set up with pores that allow fluid flow through the particles, enhancing movement of the pharmacologically active agents through the particles and/or enhancing the mucoadhesion of the mucoadhesive device. Pores may be created in the cohesive body or mucoadhesive device by incorporating a substance in the cohesive body during its preparation that may be removed or dissolved out of the matrix before administration of the device or shortly after administration. Porosity may be produced in such devices by the utilization of materials such as, but not limited to, salts such as NaCl, amino acids such as glutamine, microorganisms, enzymes, added gases (e.g. air, nitrogen, carbon dioxide . . . ), other gases caused by chemical reactions (e.g. hydrogen from hydrogen peroxide . . . ) copolymers or other materials, which will be leeched out of the mucoadhesive device to create pores.

Once the film is capable of forming a cohesive body, such a cohesive body may be formed by any of a number of methods. For example, the film may be rolled, folded, accordion-pleated, crumpled, or otherwise shaped such that the resulting cohesive body has a surface area that is less than that of the coated film. For example the film can be shaped into a cylinder, a cube, a sphere or the like. Preferably, the cohesive body is formed by rolling the coated film to form a cylinder. As previously suggested, the cohesive body may be prepared without the film step if the proper amounts of protein, mucoadhesive agent, solvent and other components are known and properly mixed to achieve the necessary characteristics of the cohesive body.

Once so formed, the cohesive body or coatable composition may be solidified prior to forming the mucoadhesive device. Such solidification occurs due to a reduction of solvent (e.g. water), which generally comprises a reduction in the bulk solvent, thereby predominantly leaving ordered solvent, such as water. For example, ordered water is normally known as water molecules that are is direct interaction with the other components of the device (e.g. protein, drug . . . ) and is not the pooling of water molecules or formation of water molecule pockets within the cohesive body or coatable composition. Many gelatins and other compositions known in the art include much bulk solvent or bulk water. The interaction between solvent molecules and other molecules are enhanced during the reduction of solvent, which is mainly due to intermolecular and intramolecular forces (i.e., ionic, dipole-dipole such as hydrogen bonding, London dispersion, hydrophobic, etc.) formed between solvent molecules, the protein molecules and the drug molecules that are strengthened upon the reduction of solvent.

The cohesive body may be solidified into a compressed matrix or spread matrix form. A compressed matrix is formed by removing bulk water from the the cohesive body by compression. Alternatively, a spread matrix form is generally solidifying the coatable composition or cohesive body utilizing one or more of solidifying techniques without applying compression to the cohesive body. It is noted that a combination of these techniques may also be utilized. Alternatives to solidify the cohesive body other than compression may be to apply heat, freeze drying, freezing to freeze fracture (e.g. liquid nitrogen, dry ice or conventional freezing) or other drying techniques to solidify the coatable composition or cohesive body before processing the coatable composition or cohesive body into mucoadhesive particles (an explanation of methods to make particles is described below).

In preparation of the mucoadhesive devices of the present invention, the cohesive body or the particles made from the solidified coatable composition or cohesive body, as will be described below, may be compressed to form a larger mucoadhesive device, such as a wafer, sphere, or cylinder.

Any manually or automatically operable mechanical, pneumatic, hydraulic, or electrical molding device capable of subjecting the cohesive body to pressure is suitable for use in the method of the present invention. In the production of various embodiments of the present invention, a molding device may be utilized that is capable of applying a pressure of from about 100 pounds per square inch (psi) to about 100,000 psi for a time period of from about 0.2 seconds to about 48 hours. Preferably, the molding device used in the method of the present invention will be capable of applying a pressure of from about 1000 psi to about 30,000 psi for a time period of from about 0.5 second to about 60 minutes. More preferably, the molding device used in the method of the present invention will be capable of applying a pressure of from about 3,000 psi to about 25,000 psi for a time period of from about 1 second to about ten minutes.

Compression molding devices suitable for use in the practice of the method of the present invention are generally known. Suitable devices may be manufactured by a number of vendors according to provided specifications, such as desirable pressure, desired materials for formulation, desired pressure source, desired size of the moldable and resulting molded device, and the like. For example, Gami Engineering, located in Mississauga, Ontario manufactures compression molding devices to specifications provided by the customer. Additionally, many compression molding devices are commercially available. See U.S. Pat. No. 6,342,250 and U.S. application Ser. No. 09/796,170, which are incorporated by reference herein, for a description of one type of compression molding device that may be utilized in the process of the present invention.

As previously suggested, the compression molding devices utilized in the process of the present invention are generally capable of applying from about 100 psi to about 100,000 psi for a time period of from about 0.2 seconds to about 48 hours, preferably capable of applying from about 1000 psi to about 30,000 psi for a time period of from about 0.5 second to about 60 minutes, and more preferably, capable of applying a pressure of from about 3000 psi to about 25,000 psi for a time period of from about 1 second to about 10 minutes.

The resulting mucoadhesive devices preferably have as little solvent as possible while still being cohesive and possessing the desired features relevant to the device's function, e.g., preferably a solvent content of from about 5% to about 60%, more preferably a solvent content of from about 10% to about 50% and most preferably 15% to 40%. It is found that when a material utilized in the production of the particles of the present invention includes one or more pharmacologically active agent, the partial drying of the film to form a cohesive body and subsequent compressing of the cohesive body, forces more solvent out of the body, thereby producing a resulting material that has a significantly higher concentration of pharmacologically active agents relative to other components of the material. As a result of the substantially uniform dispersion of a greater concentration of pharmacologically active agents, a sustained, controlled release of the pharmacologically active agent is achieved, while reducing the initial high concentration effects that can be associated with other devices that include pharmacologically active agents.

The mucoadhesive drug delivery devices of present invention may be formed into any shape and size, such as a cylinder, a tube, a wafer or any other shape that may optimize the delivery of the incorporated pharmacologically active agent.

As previously suggested, mucoadhesive devices may alternatively be derived from a solidified cohesive mass produced by solidifying the coatable composition or cohesive body by applying heat, crosslinking, freeze fracturing techniques such as liquid nitrogen freeze fracturing or dry ice freeze drying, vacuum or other similar drying techniques to eliminate excess solvent from the coatable composition or cohesive body rather than by removing the excess solvent through compression. These alternative techniques remove enough solvent from the cohesive body to provide a solidified cohesive mass that is of the proper composition and structure for the production of distinct particles. However, it is important not to eliminate too much solvent wherein the interaction of solvent and protein is lost. Embodiments of the resulting solidified cohesive mass following heating, or any of the alternative techniques identified above, usually have as little solvent as possible while still being cohesive and possessing the desired features relevant to the device's function, e.g., preferably a solvent content of from about 5% to about 60%, more preferably a solvent content of from about 10% to about 50% and most preferably 15% to 40%. As previously mentioned, the proteins, solvent and the pharmacologically active agents will interact by binding through intermolecular and intramolecular forces (i.e., ionic, dipole-dipole such as hydrogen bonding, London dispersion, hydrophobic, etc.) that are enhanced during the steps of solidifying the coatable composition or cohesive body.

One example of a method to solidify the coatable composition or cohesive body to make particles is by heating the cohesive body and then processing the resulting solidified cohesive body into mucoadhesive particles. In such a method the coatable composition or cohesive body may be dried under mild heat. In such embodiments, the coatable composition or cohesive body is heated under vacuum. It is important to note that heat should be applied so as to remove solvent and not denature or gel the cohesive body. Such gelation will inhibit the mucoadhesive qualities of the device. Generally, the heating process may be conducted under mild heat for approximately 10 seconds to 48 hours, preferably 1-24 hours and most preferably 2-6 hours per gram of coatable composition or cohesive body material. Embodiments of the resulting solidified coatable composition or cohesive body following heating, or any of the alternative techniques identified above, usually have as little solvent as possible while still being cohesive and possessing the desired features relevant to the device's function, e.g., preferably a solvent content of from about 5% to about 60%, more preferably a solvent content of from about 10% to about 50% and most preferably 15% to 40%. Once the coatable composition or cohesive body is solidified it may be processed further into particles by utilizing any particle processing technique, such as grinding or homogenizing (a description of particle processing techniques is explained below).

It is found that when a solidified coatable composition or cohesive body utilized in the production of the mucoadhesive devices of the present invention includes one or more pharmacologically active agents, the partial drying of the film to form a cohesive body and subsequent solidification of the cohesive body or the solidfication of the coatable composition, forces more solvent out of the body, thereby producing a resulting material that has a significantly higher concentration of pharmacologically active agents. As a result of the substantially uniform dispersion of a greater concentration of pharmacologically active agents, a sustained, controlled release of the pharmacologically active agent is achieved, while reducing the initial high concentration effects that can be associated with other devices that include pharmacologically active agents.

As previously suggested, particles may be derived from a solidified cohesive mass produced by solidifying the coatable composition or cohesive body by applying heat, freeze fracturing techniques such as liquid nitrogen freeze fracturing or dry ice freeze drying, vacuum or other similar drying techniques to eliminate excess solvent from the coatable composition or cohesive body rather than compressing it. It is noted that particles may also be prepared from a compressed matrix as described in the present application.

Before the solidified cohesive mass is processed into particles or after particles are produced, the cohesive body or solidified cohesive mass may also be crosslinked to provide additional beneficial characteristics. The optional step of crosslinking the mass may be performed by any means known in the art such as exposure to chemical crosslinking agents like glutaraldehyde, p-Azidobenzolyl Hydazide, N-5-Azido 2-nitrobenzoyloxysuccinimide, N-Succinimidyl 6-[4'azido-2'nitro-phenylamino]hexanoate and 4-[p-Azidosalicylamido] butylamine, applying dehydrothermal means, ultraviolet light, or other radiation sources like ultrasound, microwave or gamma radiation.

Particles utilized to prepare the mucoadhesive devices of the present invention are generally prepared by further processing the compressed matrix or solidified cohesive mass. FIG. 1 depicts embodiments of the mucoadhesive particles utilized to prepare device embodiments of the present invention. Examples of producing the particles utilized in products of the present invention include the crushing, cutting, homogenizing, pulverizing or grinding of the compressed matrix or solidified cohesive mass. In various embodiments of the present invention particles may be formed by freezing the compressed matrix or cohesive mass in liquid nitrogen and pulverizing the frozen mass, by utilizing other freeze/solid fracture or particle forming techniques or by partially heating the cohesive body until substantially rigid, but still retaining some solvent content and processing the resulting mass into particles.

In two embodiments of the present invention the particles are prepared utilizing a mill grinder or a homogenizer. Types of mill grinders and homogenizers that may be utilized include, but are not limited to ball mills, grinder stations, polytron homogeneizers and the like. One example of a polytron homogenizer that may be utilized in processing particles of the present invention may be a Polytron PT1200E purchased from the Kinematica corporation of Switzerland. An example of a ball mill that may be utilized in processing particles of the present invention may be a ball mill/roller mill purchased from U.S. Stoneware, Inc. and distributed by ER Advanced Ceramincs of Palestine, Ohio.

In another embodiment of the present invention, particles are prepared by reducing the solvent content of the coatable composition by spray drying the composition using a spray drying apparatus. The basic idea of spray drying is the production of highly dispersed particles of the present mucoadhesive material that includes all of its components from a solution or a suspension by evaporating the solvent. In this process the solution/suspension is sprayed into a hot air stream. The formed droplets have a large surface area in comparison to their volume. Since the heat transfer from the hot air to the liquid phase is proportional to the surface area, the temperature of the small droplets is raising much faster than it would do in one large drop of the same volume. This fact is important for the evaporation process: The higher the droplet temperature the faster the evaporation of the bulk solvent. The removal of a substantial amount of the bulk solvent produces a plurality of mucoadhesive particles that include a homogenous distribution of protein, mucoadhesive agent, solvent and pharmacologically active agent. An example of a spray drying device that may be utilized to prepare such particles includes, but is not limited to, the Buchig® Spray Dryer B-290, manufactured by Brinkmann Instruments, Inc., One Cantiague Road, P.O. Box 1019 Westbury, N.Y. 11590-0207. Other spray drying devices that may be utilized in the present invention may be acquired from Niro Inc., 9165 Rumsey Road, Columbia, Md. 21045.

Generally, the particles may vary in size but are normally equal to or less than 2 mm. In many embodiments of the present invention the particles are approximately 10 nm-1.75 mm, preferably 500 nm-1.5 mm and more preferably 1-1000 μm. The particles can be made to disassociate at very slow or fast rates in aqueous solutions. Another characteristic of the particles produced from the cohesive mass is that they no longer aggregate when in the particulate state. It is also noted that generally, many particle embodiments of the present invention are substantially soluble thereby allowing them to dissolve and degrade over time.

Embodiments of the resulting particles of the present invention utilizing any of the alternative techniques identified above, usually have as little solvent as possible while still being cohesive and possessing the desired features relevant to the particle's function, e.g., preferably a solvent content of from about 5% to about 60%, more preferably a solvent content of from about 10% to about 50% and most preferably 15% to 30%.

Figure 2:
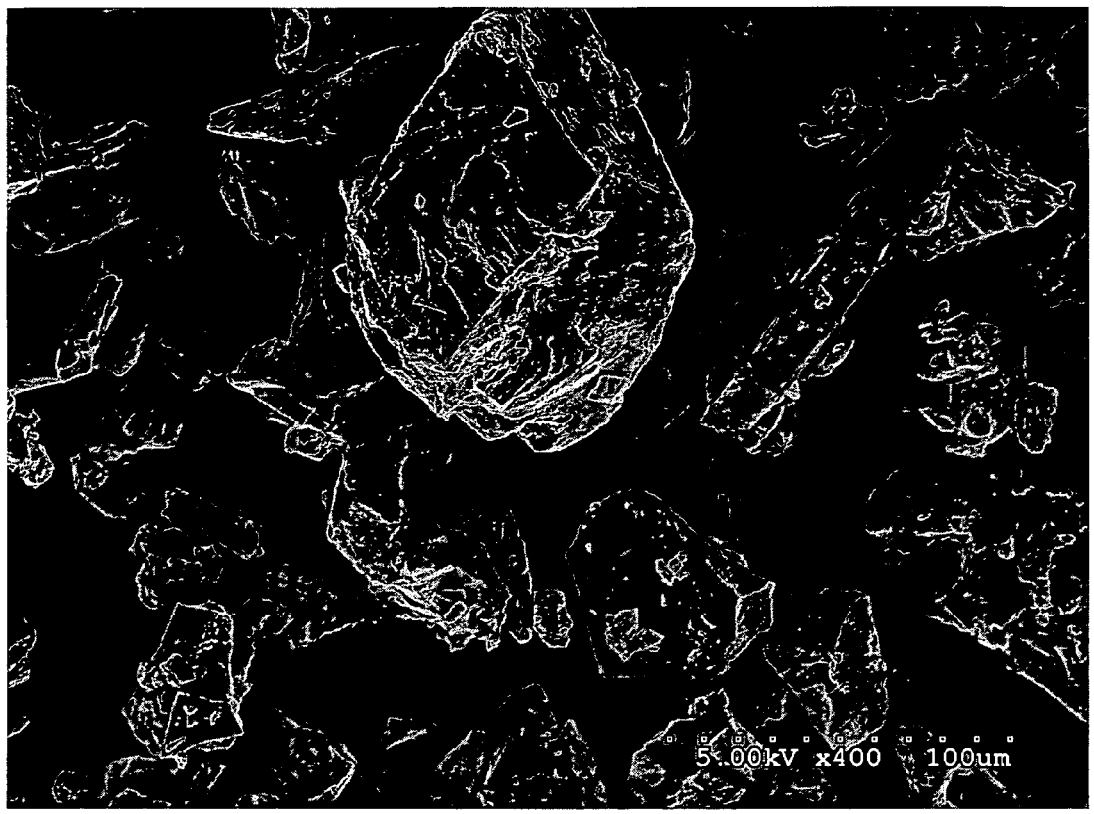
FIG. 2 depicts a scanning electron microscope (SEM) image of one embodiment of the mucoadhesive particles of the present invention at 400× magnification.
Figure 3:
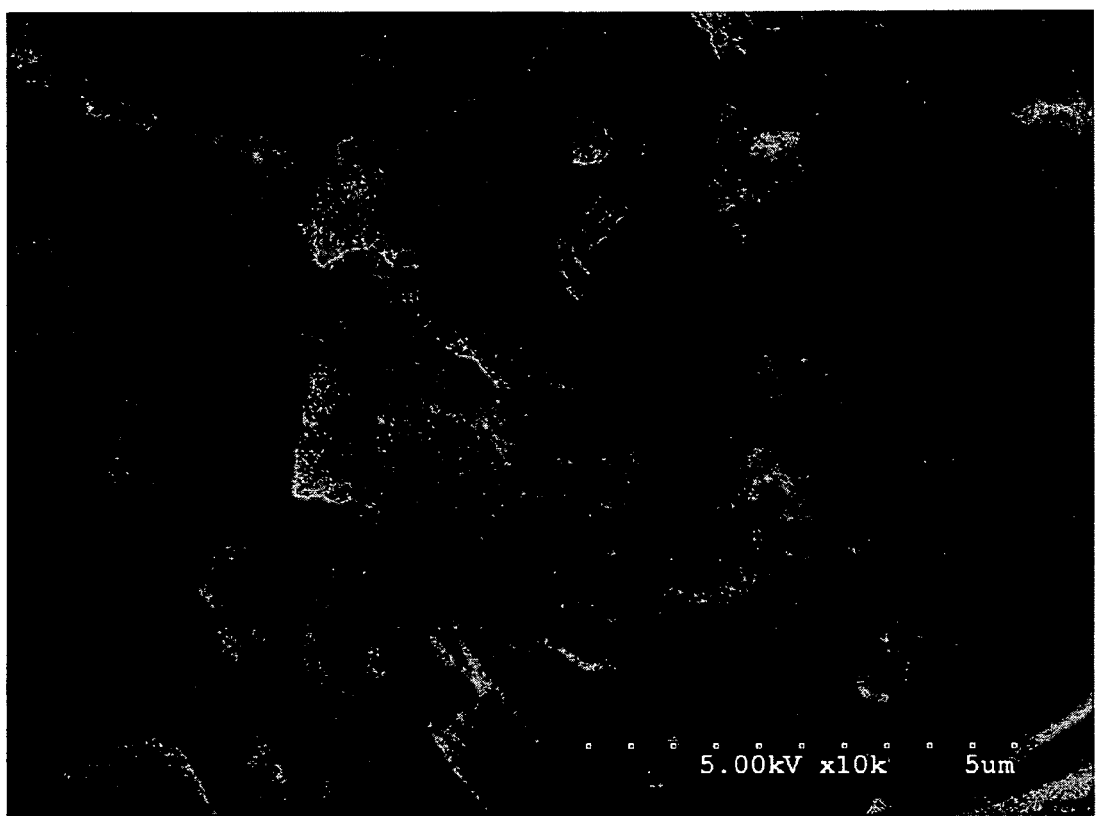
FIG. 3 depicts a scanning electron microscope (SEM) image of one embodiment of the mucoadhesive particles of the present invention at 10,000× magnification.
Figure 4:
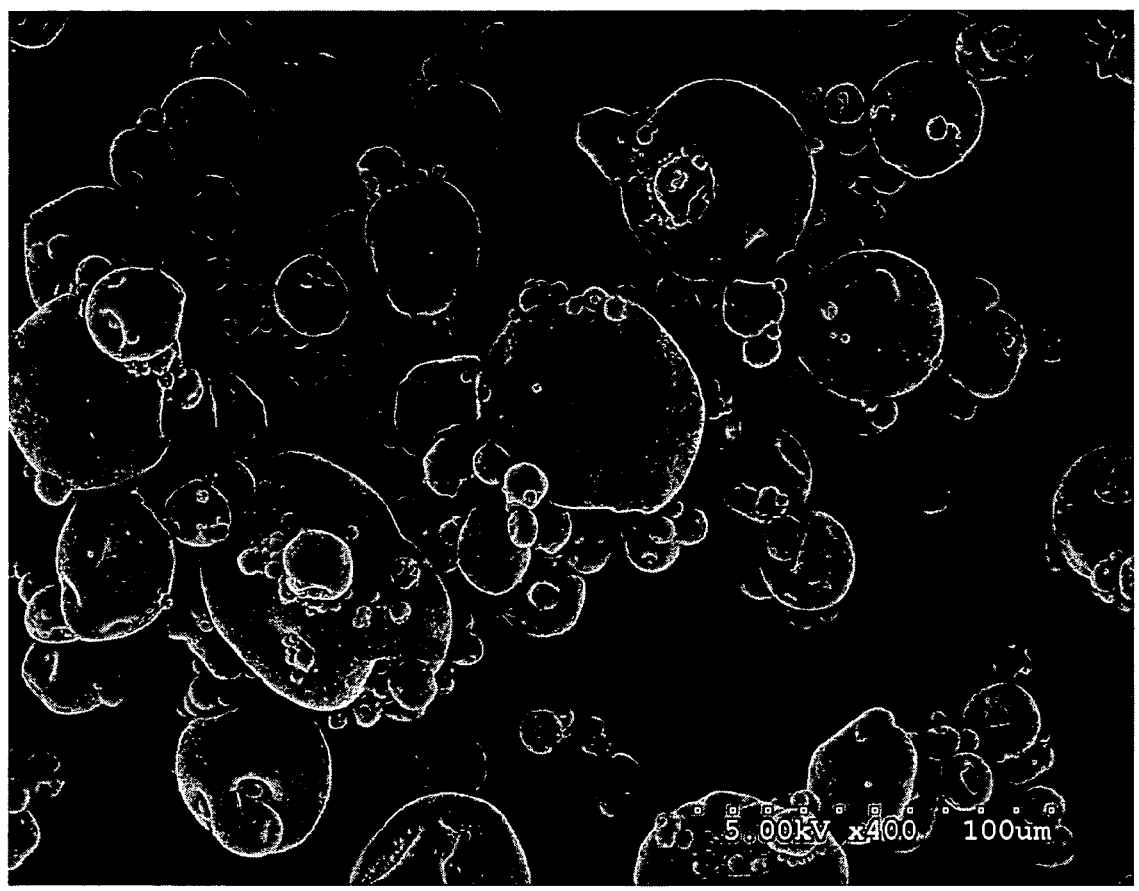
FIG. 4 depicts a scanning electron microscope (SEM) image of the albumin starting material used in one embodiment of the mucoadhesive particles of the present invention at 400× magnification.
Figure 5:
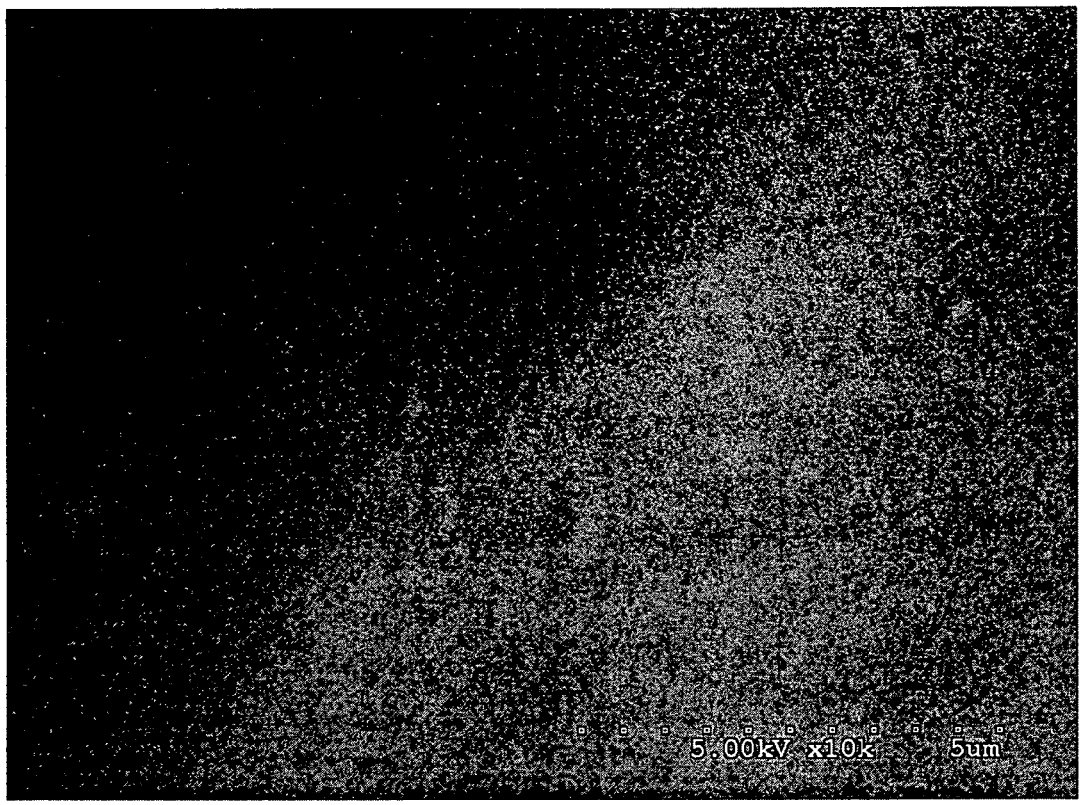
FIG. 5 depicts a scanning electron microscope (SEM) image of the albumin starting material used in one embodiment of the mucoadhesive particles of the present invention at 10,000× magnification.

FIG. 2 depicts a scanning electron microscope (SEM) image of one embodiment of the mucoadhesive particles of the present invention. As depicted in this Figure, the particles appear to possess an ordered structure of protein, solvent, mucoadhesive agent and drug due to the interaction of these components derived during fabrication. Furthermore, as depicted in FIG. 3, a closer view of the same particles of FIG. 2, the surface of this embodiment of the particles of the present invention has a rough texture and is somewhat porous. Conversely, as depicted in FIGS. 4 and 5, particles of the starting albumin material is relatively amorphous, has a smooth texture and is not porous.

After the particles are formed using the various methods described above, they may be characterized for their basic structure. First the particles may be segregated using a series of pharmaceutical drug sieves. Additional characterization of the particles will consist of verification of the shape and size of the particles using light and electron microscopy.

Also, the particles may be administered as a mucoadhesive device that adheres to mucosal tissue of the body (e.g. the buccal cavity, sublingual region, gums, gingival, palate region, the vaginal wall or the anal wall) for absorption of the pharmacologically active agent(s) through the mucosal tissue. In one embodiment of the present invention, a particle loaded saline solution or gasous particle spray may be administered as a nasal spray, mouth spray, vaginal spray or spray to any other part of the body that includes mucosal tissue. The spray is generally utilized to deliver the particles of the present invention that thereby deliver one or more pharmacologically active agents and is usually separated from any other liquid carrier (e.g. saline) until just prior to administration. It is noted that any biocompatible solution may be utilized rather than saline to deliver the particles of the present invention. This type of particulate solution or gasous spray may be administered by any means known in the art, such as a nasal spray bottle or an inhaler.

Alternatively, a mucoadhesive drug delivery device may be formed utilizing the particles. For example, particles of the present invention may be compressed into a drug delivery device in the form of a cylinder, wafer or any other suitable shape or design. For example, FIG. 1 depicts embodiments of the present invention formed in wafer and particulate form. The compression may be performed by any device known in the art, such as a conventional pill press or any of the compression devices disclosed above. Such a drug delivery device has been found to have mucoadhesive characteristics that make it optimal for sublingual, palate, vaginal, anal, gingival, or buccal drug delivery.

In one embodiment of the present invention, a coatable composition is prepared comprising one or more natural proteins, such as egg white proteins (e.g. ovalbumin), one or more biocompatible solvents such as water, one or more mucoadhesive agents such as glycerol and one or more pharmacologically active agents, such as fentanyl, capsaicin, ibuprofen, acetaminophen, desmopressen, vitamins (e.g. vitamins A, C, B1, B2, B6, B12, B12α., E, vitamin E acetate, vitamin E sorbate, K, lutein, lucopene, PABA, choline, inositol, folic, biotin, omega 3) and/or minerals (e.g. iron, selenium, calcium, copper, boron, chromium, magnesium, potassium and zinc) may be produced into a mucoadhesive drug delivery device. The solvent (e.g. water) is reduced from the coatable composition and it is next formed into a cohesive body or is solidified into a solidified cohesive mass and processed into particles. The cohesive body or particles next may be compressed into a mucoadhesive device (e.g. wafter, tablet, sphere . . . ) and adhered to the inside of the mouth, nose, vaginal cavity or anal cavity by simply applying the device to the mucosal tissue. For example, administration of such a device can be done by simply pressing the device to the mucosal tissue, such as the buccal cavity tissue, sublingual tissue, palate tissue, vaginal cavity or nasal cavity. Alternatively, the particles may be simply administered to the mucosal tissue by spraying particles into or onto such tissue (e.g. a nasal spray). The device will generally deliver the drug through the mucosal tissue without losing the drug orally or by flushing out with bodily fluids.

As previously suggested, embodiments of the mucoadhesive devices of the present invention may include mucoadhesive particles that may be combined with one or more excipients, carriers or adjuvants to form a particle formulation or composition. The excipients, carriers or adjuvants preserve the singularity of each particle in each individual dose, inhibit aggregation of particles and allow for the quick or slow dispersion of the particles once administered. For example, the rapid dispersion of the particles allows the particles to attach throughout the buccal cavity or other mucosal sites, such as lung, nasal, sublingual, intestinal, ocular, uterine, fallopian, pulmonary, stomach, vaginal, gingival, and/or rectal sites. Alternatively, the particles may be combined with an excipient, carrier or adjuvant formulation that slows the release of the particles thereby localizing them for a desired period of time or for fast release of particles to allow dispersed mucosal attachment.

Formulations or compositions suitable for use in the practice of the present invention include mucoadhesive devices (e.g. particles, sheets, wafers . . . ) formed into capsules, gels, cachets, tablets, effervescent or non-effervescent powders or tablets, powders or granules; as a solution or suspension in aqueous or non-aqueous liquid; or as an oil-in-water liquid emulsion or a water-in-oil emulsion. The compounds of the present invention may also be presented as a bolus, electuary, or paste.

Generally, formulations are prepared by uniformly mixing the particles with liquid carriers or finely divided solid carriers or both, and then if necessary shaping the product. A pharmaceutical carrier is selected on the basis of the chosen route of administration and standard pharmaceutical practice. Each carrier must be "acceptable" in the sense of being compatible with the other ingredients of the formulation and not injurious to the subject. This carrier can be a solid or liquid and the type is generally chosen based on the type of administration being used. Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g., PEG, are also preferred carriers.

The formulations for mucosal administration may comprise a non-toxic, pharmaceutically acceptable, inert carrier such as lactose, starch, sucrose, glucose, fructose, dextrose, methyl cellulose, magnesium stearate, carrageenan, dicalcium phosphate, calcium sulfate, mannitol, sorbitol, cyclodextrin, cyclodextrin derivatives, or the like.

Capsules or tablets can be easily formulated and can be made easy to administer to the buccal cavity or other mucosal sites. Tablets may contain other suitable carriers, binders, lubricants, diluents, disintegrating agents, coloring agents, flavoring agents, flow-inducing agents, or melting agents. A tablet may be made by compression or molding the mucoadhesive particles, cohesive body or cohesive mass of the present invention, optionally with one or more additional materials (e.g. carriers, binders, lubricants, diluents, disintegrating agents, coloring agents . . . ). As previously suggested, compressed tables may be prepared by compressing the particles, cohesive body or cohesive mass in a free flowing form (e.g., powder, granules) optionally mixed with a binder (e.g., gelatin, hydroxypropylmethylcellulose, povodone, carbocol, polyvinylalcohol), lubricant, inert diluent, preservative, disintegrant (e.g., sodium starch glycolate, cross-linked carboxymethyl cellulose) surface-active or dispersing agent. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, or the like. Lubricants used in these dosage forms include sodium oleate, sodium stearate, magnesium stearate, sodium benzoate, sodium acetate, sodium chloride, or the like. Disintegrators include, for example, starch, methyl cellulose, agar, bentonite, xanthan gum, or the like. In one example, molded tablets may be made by molding in a suitable machine a mixture of the mucoadhesive particles of the present invention moistened with an inert liquid diluent (e.g. solvent, such as water, mucoadhesive agent such as glycerol . . . ).

The tablets may optionally be coated or scored and may be formulated so as to provide slow- or controlled-release of the active ingredient. The coatings may be utilized to retain the particles while passing through the oral tract and into the stomach. Tablets may also optionally be provided with an enteric coating to provide release in parts of the gut other than the stomach. Additionally, the tablets may be coated on one side to act as a dissolution barrier when the opposite side is attached to the mucosal tissue.

Exemplary pharmaceutically acceptable carriers and excipients that may be used to formulate oral dosage forms of the present invention are described in U.S. Pat. No. 3,903,297 to Robert, issued Sep. 2, 1975, or the Handbook of Pharmaceutical Excipients, by Arthur H. Kibbe(Editor), Ainley Wade and Paul J. Weller, Amer. Pharmaceutical Assoc.; 3rd edition (Jan. 15, 2000), both of which are incorporated by reference herein in their entirety. Techniques and compositions for making dosage forms useful in the present invention are described in the following references: 7 Modem Pharmaceutics, Chapters 9 and 10 (Banker & Rhodes, Editors, 1979); Lieberman et al., Pharmaceutical Dosage Forms: Tablets (1981); and Ansel, Introduction to Pharmaceutical Dosage Forms 2nd Edition (1976).

In addition to the mucoadhesive proteins and the biocompatible solvent(s), the particles or devices made from the particles of the present invention advantageously may themselves incorporate other drug delivery devices that would otherwise typically migrate away from the desired delivery site and/or are potentially undesirably reactive with surrounding bodily fluids or tissues. Such migration is undesirable in that the therapeutic effect of the pharmacological agents encapsulated therein may occur away from the desired site, thus eliminating the advantage of localized delivery or enhanced absorption. When a drug delivery device incorporating a migration-vulnerable and/or reactive drug delivery device (hereinafter referred to as a "two-stage drug delivery device") is subsequently implanted, attached and/or administered, the migration-vulnerable and/or reactive drug delivery device(s) is/are held in place and protected by the two-stage mucoadhesive device. Then, as the material of the migration-vulnerable drug delivery devices degrade or dissolve, thereby releasing the pharmacologically active agents incorporated therein, the pharmacologically active agents diffuse through and/or release from the mucoadhesive device of the two-stage drug delivery device. Furthermore, the mucoadhesive device reduces, if not prevents, the potential for undesirable reaction with bodily fluids or tissues that may otherwise occur upon implantation, application or administration of a reactive drug delivery device. Examples of such drug delivery devices subject to migration for the delivery site include, but are not limited to, particles, vesicles, e.g., liposomes, liposheres and microspheres.

Vesicles are made up of microparticles or colloidal carriers composed of lipids, carbohydrates or synthetic polymer matrices and are commonly used in liquid drug delivery devices. Vesicles, for example, have been used to deliver anesthetics using formulations with polylactic acid, lecithin, iophendylate and phosphotidyl choline and cholesterol. For a discussion of the characteristics and efficiency of drug delivery from vesicles, see, e.g., Wakiyama et al., *Chem., Pharm. Bull.*, 30, 3719 (1982) and Haynes et al., *Anesthiol*, 74, 105 (1991), the entire disclosures of which are incorporated by reference herein.

Liposomes, the most widely studied type of vesicle, can be formulated to include a wide variety of compositions and structures that are potentially non-toxic, biodegradable and non-immunogenic. Furthermore, studies are in progress to create liposomes that release more drug in response to changes in their environment, including the presence of enzymes or polycations or changes in pH. For a review of the properties and characteristics of liposomes see, e.g., Langer, *Science*, 249, 1527 (1990); and Langer, *Ann. Biomed. Eng.*, 23, 101 (1995), the entire disclosures of which are incorporated by reference herein.

Liposheres are an aqueous microdispersion of water insoluble, spherical microparticles (from about 0.2 to about 100 um in diameter), each consisting of a solid core of hydrophobic triglycerides and drug particles that are embedded with phospholipids on the surface. Liposheres are disclosed in U.S. Pat. No. 5,188,837, issued to Domb, the disclosure of which is incorporated herein by reference.

Microspheres typically comprise a biodegradable polymer matrix incorporating a drug. Microspheres can be formed by a wide variety of techniques known to those of skill in the art. Examples of microsphere forming techniques include, but are not limited to, (a) phase separation by emulsification and subsequent organic solvent evaporation (including complex emulsion methods such as oil in water emulsions, water in oil emulsions and water-oil-water emulsions); (b) coacervation-phase separation; (c) melt dispersion; (d) interfacial deposition; (e) in situ polymerization; (f) spray drying and spray congealing; (g) air suspension coating; and (h) pan and spray coating. These methods, as well as properties and characteristics of microspheres are disclosed in, e.g., U.S. Pat. Nos. 4,652,441; 5,100,669; 4,526,938; WO 93/24150; EPA 0258780 A2; U.S. Pat. Nos. 4,438,253; and 5,330,768, the entire disclosures of which are incorporated by reference herein.

Inasmuch as the migration-vulnerable and/or reactive particles or devices made of such particles will desirably further encapsulate a pharmacologically active agent, the amount of these devices to be utilized in the two-stage drug delivery device may be determined by the dosage of the pharmacologically active agent, as determined as described hereinabove. The amount of migration-vulnerable and/or reactive drug delivery devices to be included in the particles or device made of such particles of the present invention desirably ranges from about 10 to about 1 billion, more preferably ranges from about 10,000 to about 500 million, and most preferably ranges from about 1 million to about 200 million.

Other embodiments of the mucoadhesive drug delivery devices of the present invention may include a plurality of layers. For example, a multi-layered drug delivery device may comprise alternating layers of mucoadhesive material that have drug release additives, which inhibit and/or enhance the release of drugs. These layers may be arranged to manage the directional flow of drugs to a desired site. Alternatively, alternating layers may include different amounts of the same pharmacologically active agents or the alternating layers may include different pharmacologically active agents that are laminated together to form the mucoadhesive drug delivery device.

The previous description has disclosed and suggested various embodiments related to the preparation and administration of the mucoadhesive devices of the present invention. As previously mentioned, the devices of the present invention provide optimum tissue residency time for delivery of the pharmacologically active agents, but furthermore dissolve/degrade and disappear upon delivery of the such agents. The disappearance of such devices without inconvenience, discomfort or adverse reaction is an important feature of the present devices. For example, the preparation of such devices with soluble proteins that are common in food products provide beneficial dissolving and/or degradation of the devices once they have delivered their active agents. Generally, the mucoadhesive devices will remain adhered to the mucosal tissue for approximately 2 min. to 16 hours per 125 mg/cm$^2$, preferable about 5 min. to 2 hours per 125 mg/cm$^2$ and more preferably from about 10 min. to 1 hour per 125 mg/cm$^2$. In a few embodiments of the present invention devices comprising ovalbumin, glycerol, water and a drug adhered comfortably and was unmovable from the buccal surface with the tongue. These embodiments melted away without notice in approximately 3 minutes for the fast dissolve formulation and in approximately 15 to 30 minutes for the slow dissolve formulations. In another example such wafers have been found to immediately attach to a wetted finger and stay attached after submersion into 37° C. saline while it melts away completely without detaching. This has demonstrated the ability for a wafer of the mucoadhesive material to have adequate strength to stay attached and hold together for a desired time when placed in an aqueous environment.

Furthermore, it has been found that in many embodiments of the present invention, the mucoadhesive devices and particles have mucoadhesive tensile strengths (corrected for technique and preparation (an example of which is found in tables 1-3)) that are approximately greater than 0.01 N/cm$^2$, optionally greater than 0.05 N/cm$^2$ or optionally greater than 0.15 N/cm$^2$ or optionally greater than 0.30 N/cm$^2$.

EXAMPLE I

Mucoadhesive Composition

Powdered egg albumin (Alfachem) (50 gs) is added to a stirred (magnetic stirrer) solution of glycerol (15 gs) in saline (0.9%) (187.5 mls) in a 500 ml beaker. After all the albumin has been added, and mostly dispersed, the solution is shaken at the slow settting for 30 minutes on a platform shaker (Eberbach). (note: an active drug may be added to the glycerol/saline solution before the albumin is added). The resulting solution/dispersion was divided into two-250 ml beakers up to the 125 ml mark (approximately one-half full). The two beakers were covered with foil and placed in a freezer at −20° C. overnight. The frozen solutions were next placed onto a freeze-drier platform previously held at −30° C. and left to equilibrate for one hour. Cooling of the platform was then discontinued when a vacuum of 200 millitor was obtained. The condenser was then turned off. Full vacuum was then continued for 48 hours or until the platform temperature reached ambient (25° C. on the temperature dial). The resulting freeze-dried solid was then removed and ground for one hour using a ceramic ball mill (2 cm×2 cm media) and roller mill set at 35 rpm. The final milled product was passed through a 150 µ sieve to yield 40 gs of a slightly yellow, fine mucoadhesive particles. (It is noted that portions of the particles were compressed into uniform wafers (approximately 6 mm in diameter, 50, 100 and 150 mg) using a pneumatic press. Such wafers produced buccal residence time when tested in vivo of 3 min., 10 min. and 20 min. respectively)

EXAMPLE II

In Vitro Bioadhesion Tests on Mucosal Tissue

Mucoadhesive devices including ovalbumin, glycerol and water (no drug) were made into particles utilizing the methods described above. 150 mg of the particles were compressed into 1 cm diameter wafers at 1375 psi for 3 min (MAD1, MAD 2 and MAD3). The wafers were then tested for mucoadhesive attachment by adhering them to the bottom of a glass beaker with double sided Scotch®, 3M tape and pressing the bottom of the beaker to fresh wetted mucosal membrane from pig intestine that was cleaned for usage in sausage casing. The bottom of the beaker was pressed to the mucosal membrane for 30 seconds at approximately 10 psi. The beaker was then placed on a Satorius electronic balance and the membrane pulled slowly in an upward motion at a 45° angle away from the wafer and beaker until completely detached. The measurement taken was the detachment force, which is the difference between the starting weight of the beaker, wafer and membrane and the lowest weight registered on the scale during the removal of the membrane. Similar measurements were also taken of mucoadhesive wafers heated at 120° C., sodium alginate powder compressed into wafers at 1375 psi for 3 min, 1 cm wetted collagen gel wafers and the glass beaker as control for pig intestine adhesion. The following table (Table 1) discloses the mucoahesive results of an average of three wafers of each type:

TABLE 1

Results from Mucoadhesive Devices (MAD) (tensile stress (N/cm2)

| Contact Time (s) | MAD[a] (N/cm$^2$) | Heated MAD[a] (N/cm$^2$) | Sodium Alginate[a] (N/cm$^2$) | Collagen Gel[a] (N/cm$^2$) | Glass Beaker[a] (N/cm$^2$) |
|---|---|---|---|---|---|
| 30 | 0.38 | 0.03 | 0.08 | <0.01 | <0.01 |

[a](average, n = 3)

EXAMPLE III

In Vitro Bioadhesion Tests on Mucosal Tissue

Mucoadhesive devices including ovalbumin, glycerol and water were made into wafers and were tested for mucoadhesive attachment to fresh mucosal membrane from pig intestine by Christer Nyström, Ph.D., of the University of Uppsala, Uppsala, Sweden. A TA-HDi texture analyser (Stable Micro Systems, Haslemere, UK) with a 5 kg load cell was used. The pig intestine was cut into approximately 2 cm$^2$ pieces and placed in a tissue holder. The mucoadhesive devices were attached to the upper probe using double-sided tape (Scotch, 3M). After spreading 3 ml of buffer [Krebs-Ringer Bicarbonate] with a pipette onto mucosa, the studied material was brought into contact with mucosa under a force of 0.5 N over 30 seconds. The probe was then raised at a constant speed of 0.1 mm/s and the detachment force was recorded as a function of displacement. The detachment force was measured at a sampling rate of 25 measurements/second throughout the measuring cycle and the maximum force was determined using computer software. The tensile stress (N/cm2) was obtained by dividing detachment force by area of the mucoadhesive wafer or probe. The work of adhesion was calculated from the area under the curve of tensile stress versus probe displacement.

The tensile stress and the work of adhesion for the tested mucoahesive devices and the probe are presented in Table 2. In table 3 results for materials used in a previous study are shown (Bredenberg, S. Nyström, C, (2002), In vitro evaluation of bioadhesion in particulate systems and possible improvement using interactive mixtures, J. Pharm Pharmacol). In this study, taking into account all data generated for tablets, powders and mixtures, there seemed to be a maximum tensile stress of approximately 1.5 N/cm2. This value of 1.5 N/cm2 reflected the intrinsic strength of the mucus layer since that would be the strongest part of the system in this study. Lower tensile stress values would then reflect a weakening of the bioadhesive joint.

For dry powders and tablets, dehydration of mucosa is a possible mechanism for bioadhesion. This mechanism is caused by water movement from mucosa to the dry powder, resulting in adhesion between the two surfaces. Another mechanism is adhesion forces due to surface tension created between the mucosa and material. Attraction forces due to surface energy effects have also been identified as a possible bioadhesive mechanism. Since the metal probe used as a control had rather high tensile stress and work, probably due to surface tension and/or attraction forces, powders of mannitol is a better control reference since it has no bioadhesive properties (Table 3). Compared to mannitol, the mucoadhesive devices had significant bioadhesive properties and could be compared to interactive mixtures of mannitol+Ac-Di-Sol and Emcompress (DCP)+Ac-Di-Solg® (DCP=Dicalcium Phosphate; Ac-Di-Sol®=ADS=a modified cellulose gum) (Table 3). These results indicate that the mucoadhesive devices are comparable to the interactive mixtures (especially DCP+Ac-Di-Solg®) used in the study by Bredenberg and Nyström (2002), but slightly less to tablets of sodium alginate, a well-known strong bioadhesive material. However, even though highly bioadhesive, sodium alginate also dissolves very rapidly in an aqueous environment, thereby rendering it relatively ineffective as a mucoadhesive drug delivery device.

TABLE 2

Results from Mucoadhesive Devices (MAD) (tensile stress (N/cm2) and tensile work (mJ/cm2)

| Contact Time (s) | MAD 1 (N/cm$^2$) | MAD 2 (N/cm$^2$) | MAD 3 (N/cm$^2$) | Probe[a] (N/cm$^2$) | MAD 1 (mJ/cm$^2$) | MAD 2 (mJ/cm$^2$) | MAD 3 (mJ/cm$^2$) | Probe[a] (mJ/cm$^2$) |
|---|---|---|---|---|---|---|---|---|
| 30 | 0.736 | 0.633 | 0.933 | 0.407 | 0.058 | 0.052 | 0.075 | 0.032 |

[a](average, n = 3)

TABLE 3

Results from a previous study (tensile stress (N/cm$^2$) and tensile work (mJ/cm$^2$)

| Contact Time (s) | Mannitol[a] (N/cm$^2$) | Mixture[a] Mannitol + ADS (N/cm$^2$) | Mixture[a] DCP + ADS (N/cm$^2$) | Sodium Alginate Tablets (N/cm$^2$) | Mannitol[a] (mJ/cm$^2$) | Mixture[a] Mannitol + ADS (mJ/cm$^2$) | Mixture[a] DCP + ADS (mJ/cm$^2$) | Sodium Alginate Tablet. (mJ/cm$^2$) |
|---|---|---|---|---|---|---|---|---|
| 30 | 0.017 | 0.284 | 0.845 | 1.44 | 0.015 | 0.032 | 0.102 | .182 |

[a](average, n = 5)

The results of Table 1 and Tables 2 and 3 differ for the absolute tensile stress measurements due to the difference between cleaned (Table 1) and fresh, untouched (Table 2 and 3) pig intestine and due to pig intestine detachment angle techniques (Table 1 45° and Table 2 and 3 0°). Therefore, the values are best compared after being corrected by subtracting the probe or the beaker glass tensile stress, which is a correction for the mucoadhesive property variation due to different pig intestine batches and handling and also a correction for the detachment angle.

While the invention has been described in conjunction with specific embodiments thereof, it is evident that many alternatives, modifications, and variations will be apparent to those

The invention claimed is:

1. A mucoadhesive device, comprising one or more purified free-form proteins, wherein one of the purified proteins included in the mucoadhesive device is ovalbumin, combined with one or more pharmacologically active agents, one or more mucoadhesive agents and one or more biocompatible solvents formed into a cohesive body or solidified cohesive mass that is formed into a mucoadhesive device and having the purified proteins in an amount of about 15% to 85% by weight of the mucoadhesive device, and the mucoadhesive agents in an amount of about 0.1% to 35% by weight of the mucoadhesive device, wherein the mucoadhesive device is configured to have a form such that the mucoadhesive device is capable of adhering to mucosal tissue of a patient for the delivery of the one or more pharmacologically active agents to the patient.

2. The mucoadhesive device of claim 1, wherein the mucoadhesive device further includes one or more additional purified proteins selected from the group consisting of elastin, collagen, albumin, plakalbumin, lactalbumin, glycomacropeptide, lactoglobulin, prealbumin, glutamine oligopeptide, casein, keratin, fibronectin, silk, silk fibroin, actin, myosin, fibrinogen, thrombin, aprotinin, antithrombin III, whey protein, betalactoglobulin, alphlactalbumin, rice protein, grape vine protein, grape leaf protein, maize protein, olive protein, canola protein, soy protein, cottonseed protein, cotton leaf protein, seaweed protein, wheat protein, agglutinen, tobacco proteins, F1 and F2 protein, chickpea protein, fish protein and combinations thereof.

3. The mucoadhesive device of claim 1, wherein the biocompatible solvent is selected from the group consisting of water; saline; dimethyl sulfoxide (DMSO); methanol, ethanol, formic acid, olive oil, peanut oil and combinations thereof.

4. The mucoadhesive device of claim 3, wherein the biocompatible solvent is water.

5. The mucoadhesive device of claim 1, wherein the mucoadhesive agents are selected from the group consisting of glycerol, pectin, polyethylene glycol, sorbitol, maltitol, mannitol, hydrogenated glucose syrups, xylitol, polydextrose, glyceryl triacetate, propylene glycol, propylene glycol alginate, glycogen and combinations thereof.

6. The mucoadhesive device of claim 1, wherein the mucoadhesive agent is glycerol.

7. The mucoadhesive device of claim 1, further including an additive wherein the additive is selected from the group consisting of polyurethanes, vinyl homopolymers and copolymers, acrylate homopolymers and copolymers, polyethers, cellulosics, epoxies, polyesters, acrylics, nylons, silicones, polyanhydride, poly(ethylene terephthalate), polyacetal, poly(lactic acid), poly(ethylene oxide)/poly(butylene terephthalate) copolymer, polycarbonate, poly(tetrafluoroethylene) (PTFE), polycaprolactone, polyethylene oxide, poly (vinyl chloride), polylactic acid, polyglycolic acid, polypropylene oxide, poly(akylene)glycol, polyoxyethylene, sebacic acid, polyvinyl alcohol (PVA), 2-hydroxyethyl methacrylate (HEMA), polymethyl methacrylate, 1,3-bis(carboxyphenoxy)propane, lipids, phosphatidylcholine, triglycerides, polyhydroxybutyrate (PHB), polyhydroxyvalerate (PHV), poly(ethylene oxide) (PEO), poly ortho esters, poly (amino acids), polycynoacrylates, polyphophazenes, polysulfone, polyamine, poly (amido amines), fibrin, graphite, flexible fluoropolymer, isobutyl-based, isopropyl styrene, vinyl pyrrolidone, cellulose acetate dibutyrate, silicone rubber, ceramics, bioceramics, glasses bioglasses, glass-ceramics, resin cement, resin fill, glass ionomer, hydroxyapatite, calcium sulfate, $Al_2O_3$, tricalcium phosphate, calcium phosphate salts, sugars, starches, carbohydrates, salts, polysaccharides, alginate, carbon, cobalt-based alloys, galvanic-based alloys, stainless steel-based alloys, titanium- based alloys, zirconium oxide, zirconia, silica, aluminum-based alloys, vanadium-based alloys, molybdenum-based alloys, nickel-based alloys, iron-based alloys, zinc phosphate, zinc polycarboxylate and combinations thereof.

8. The mucoadhesive device of claim 1, wherein the pharmacologically active agent is selected from the group consisting of proteins, peptides, polysaccharides, nucleic acids, oligonucleotides, steroids, cytotoxic agents, analgesics, anti-inflammatories, anesthetics, aminoglycosides, dermatological agents, antiviral, antibiotics, antimicrobials, vesicles, antibodies, vitamins, cofactors, viruses, microorganisms, cells, blood clotting factors, clot inhibitors, clot dissolving agents, tissues, antiestrogens, antigens, antiandrogens, muscle relaxants, prostaglandins, iodine compounds, nutritional agents, allergens, protease inhibitors, antirheumatoid agents, obstetric drugs, ovulation inducers, diuretics, antidiuretics, antihistamines, ceramides, antifungals, quinolones, sulfa drugs, neuromuscular blocking agents, anticonvulsants, CNS stimulants, antianxiety drugs, neuroleptics, antidepressants, sedatives, hemostatic agents, vasodilators, adrenergic stimulants, antimigraine drugs, cardiotonic glycosides, beta-adrenergic blocking agents, antiangina agents, antiarrhythmics, calcium channel blockers, sodium channel blockers, antihypertensives, anticoagulants, thrombolytic agents, antipyretics, anti-alzheimer's agents, anti-Parkinson's agents, antiemetics, reductase inhibitors, pituitary hormones, thyroid hormones, hypoglycemic agents, hormones, antimalarials, anoretic agents, hypercalcemia, antitussives, expectorants, decongestants, bronchospasm relaxants, smoking cessation agents, vaccines and any combination or prodrugs thereof.

9. The mucoadhesive device of claim 1, wherein the one or more purified proteins is ovalbumin, the one or more biocompatible solvents is water and the one or more mucoadhesive agents is glycerol.

10. The mucoadhesive device of claim 9, wherein the one or more pharmacologically active agents are selected from the group consisting of peptides, antisense, anesthetics, analgesics, chemotherapy agents, antidiuretics, anti-inflammatories and neurotoxins.

11. The mucoadhesive device of claim 1, wherein the one or more biocompatible solvents are selected from the group consisting of water, saline and DMSO.

12. The mucoadhesive device of claim 1, wherein the cohesive body is compressed and formed into a wafer, tablet, cylinder, sheet or sphere.

13. The mucoadhesive device of claim 1, wherein the cohesive body is compressed and processed into particles.

14. The mucoadhesive device of claim 1, wherein the solidified cohesive mass is processed into particles.

15. The mucoadhesive device of claim 14, wherein a plurality of the particles are compressed into a mucoadhesive mass.

16. The mucoadhesive device of claim 15, wherein the mass is a tablet, sphere, cylinder, sheet or wafer.

17. A mucoadhesive device, comprising ovalbumin in a free-form state, combined with one or more pharmacologically active agents, one or more mucoadhesive agents and one or more biocompatible solvents and formed into a cohesive body or solidified cohesive mass that is formed into a mucoadhesive device having a homogenous distribution of the ovalbumin in an amount of about 15% to 85% by weight of the mucoadhesive device, pharmacologically active agents, mucoadhesive agents in an amount of about 0.1% to 35% by weight of the mucoadhesive device and biocompatible solvents, wherein the mucoadhesive device is configured to have a form such that the mucoadhesive device is capable of adhering to mucosal tissue of a patient for the delivery of the one or more pharmacologically active agents to the patient.

18. The mucoadhesive device of claim 17, wherein the biocompatible solvent is selected from the group consisting of water; saline; dimethyl sulfoxide (DMSO);

methanol, ethanol, formic acid, olive oil, peanut oil and combinations thereof.

19. The mucoadhesive device of claim 18, wherein the biocompatible solvent is water.

20. The mucoadhesive device of claim 17, wherein the mucoadhesive agents are selected from the group consisting of glycerol, pectin, polyethylene glycol, sorbitol, maltitol, mannitol, hydrogenated glucose syrups, xylitol, polydextrose, glyceryl triacetate, propylene glycol, propylene glycol alginate, glycogen and combinations thereof.

21. The mucoadhesive device of claim 20, wherein the mucoadhesive agents is glycerol.

22. The mucoadhesive device of claim 17, further including an additive wherein the additive is selected from the group consisting of polyurethanes, vinyl homopolymers and copolymers, acrylate homopolymers and copolymers, polyethers, cellulosics, epoxies, polyesters, acrylics, nylons, silicones, polyanhydride, poly(ethylene terephthalate), polyacetal, poly(lactic acid), poly(ethylene oxide)/poly(butylene terephthalate) copolymer, polycarbonate, poly(tetrafluoroethylene) (PTFE), polycaprolactone, polyethylene oxide, poly (vinyl chloride), polylactic acid, polyglycolic acid, polypropylene oxide, poly(akylene)glycol, polyoxyethylene, sebacic acid, polyvinyl alcohol (PVA), 2-hydroxyethyl methacrylate (HEMA), polymethyl methacrylate, 1,3-bis(carboxyphenoxy)propane, lipids, phosphatidylcholine, triglycerides, polyhydroxybutyrate (PHB), polyhydroxyvalerate (PHV), poly(ethylene oxide) (PEO), poly ortho esters, poly (amino acids), polycynoacrylates, polyphophazenes, polysulfone, polyamine, poly (amido amines), fibrin, graphite, flexible fluoropolymer, isobutyl-based, isopropyl styrene, vinyl pyrrolidone, cellulose acetate dibutyrate, silicone rubber, ceramics, bioceramics, glasses bioglasses, glass-ceramics, resin cement, resin fill, glass ionomer, hydroxyapatite, calcium sulfate, $Al_2O_3$, tricalcium phosphate, calcium phosphate salts, sugars, starches, carbohydrates, salts, polysaccharides, alginate, carbon, cobalt-based alloys, galvanic-based alloys, stainless steel-based alloys, titanium-based alloys, zirconium oxide, zirconia, silica, aluminum-based alloys, vanadium-based alloys, molybdenum-based alloys, nickel-based alloys, iron-based alloys, zinc phosphate, zinc polycarboxylate and combinations thereof.

23. The mucoadhesive device of claim 17, wherein the pharmacologically active agent is selected from the group consisting of proteins, peptides, polysaccharides, nucleic acids, oligonucleotides, steroids, cytotoxic agents, analgesics, antiinflammatories, anesthetics, aminoglycosides, dermatological agents, antiviral, antibiotics, antimicrobials, vesicles, antibodies, vitamins, cofactors, viruses, microorganisms, cells, blood clotting factors, clot inhibitors, clot dissolving agents, tissues, antiestrogens, antigens, antiandrogens, muscle relaxants, prostaglandins, iodine compounds, nutritional agents, allergens, protease inhibitors, antirheumatoid agents, obstetric drugs, ovulation inducers, diuretics, antidiuretics, antihistamines, ceramides, antifungals, quinolones, sulfa drugs, neuromuscular blocking agents, anticonvulsants, CNS stimulants, antianxiety drugs, neuroleptics, antidepressants, sedatives, hemostatic agents, vasodilators, adrenergic stimulants, antimigraine drugs, cardiotonic glycosides, beta-adrenergic blocking agents, antiangina agents, antiarrhythmics, calcium channel blockers, sodium channel blockers, antihypertensives, anticoagulants, thrombolytic agents, antipyretics, anti-alzheimer's agents, anti-Parkinson's agents, antiemetics, reductase inhibitors, pituitary hormones, thyroid hormones, hypoglycemic agents, hormones, antimalarials, anoretic agents, hypercalcemia, antitussives, expectorants, decongestants, bronchospasm relaxants, smoking cessation agents, vaccines and any combination or prodrugs thereof.

24. The mucoadhesive device of claim 17, wherein the one or more biocompatible solvents is water and the one or more mucoadhesive agents is glycerol.

25. The mucoadhesive device of claim 17, wherein the one or more pharmacologically active agents are selected from the group consisting of peptides, antisense, anesthetics, analgesics, chemotherapy agents, antidiuretics, anti-inflammatories and neurotoxins.

26. The mucoadhesive device of claim 17, wherein the cohesive body is compressed.

27. The mucoadhesive device of claim 16, wherein the compressed cohesive body is formed into a wafer, tablet, cylinder, sheet or sphere.

28. The mucoadhesive device of claim 17, wherein the compressed cohesive body is processed into particles.

29. The mucoadhesive device of claim 17, wherein the solidified cohesive mass is processed into particles.

30. The mucoadhesive device of claim 28, wherein a plurality of the particles are compressed into a tablet, sphere, cylinder, sheet or wafer.

31. The mucoadhesive device of claim 29, wherein a plurality of the particles are compressed into a tablet, sphere, cylinder, sheet or wafer.

32. A method of delivering one or more pharmacologically active agents through the mucosal tissue of a patient comprising the steps of:
adhering a mucoadhesive device to the mucosal tissue of a patient, said mucoadhesive device including one or more purified free-form proteins, wherein one of the purified proteins included in the mucoadhesive device is ovalbumin, combined with one or more pharmacologically active agents, one or more mucoadhesive agents and one or more biocompatible solvents to form a coatable composition, wherein the solvent content of the coatable composition is reduced and formed into a mucoadhesive device having a homogenous distribution of the purified proteins, pharmacologically active agents, mucoadhesive agents and biocompatible solvents, wherein the mucoadhesive device is configured to have a form such that the mucoadhesive device adheres to the mucosal tissue of the patient for the delivery of the one or more pharmacologically active agents to the patient.

33. The method of delivering one or more pharmacologically active agents through mucosal tissue of a patient of claim 32, wherein the mucosal tissue is located at the cheek, gum, sublingual area, palate, tongue, periodontal pockets, nasal cavity, vaginal cavity, anal cavity, intestinal walls, pulmonary regions, ocular areas, or stomach cavity.

34. The method of delivering one or more pharmacologically active agents through mucosal tissue of a patient of claim 32, wherein the one or more biocompatible solvents is water and the one or more mucoadhesive agents is glycerol.

35. The method of delivering one or more pharmacologically active agents through mucosal tissue of a patient of claim 32, wherein the one or more pharmacologically active agents are selected from the group consisting of peptides, antisense, anesthetics, analgesics, chemotherapy agents, antidiuretics, anti-inflammatories, neurotoxins and vitamins.

36. The method of delivering one or more pharmacologically active agents through mucosal tissue of a patient of claim 32, where the mucoadhesive device is in a form selected from the group consisting of a wafer, tablet, cylinder, sheet, particles or sphere.

37. A method of making a mucoadhesive drug delivery device comprising:
(a) preparing a coatable composition including one or more biocompatible purified free-form proteins, wherein one of the purified proteins included in the mucoadhesive device is ovalbumin, one or more biocompatible solvents, one or more mucoadhesive agents and one or more pharmacologically active agents;
(b) partially drying the coatable composition to reduce bulk solvent present in the system to form a solidified cohesive mass including a substantially homogenous distribution of purified proteins, solvents, mucoadhesive agents and pharmacologically active agents; and
(c) processing the cohesive mass to form a mucoadhesive device, wherein the mucoadhesive device is processed to have a form such that the mucoadhesive device is capable of adhering to mucosal tissue of a patient for the delivery of the one or more pharmacologically active agents to the patient.

38. The method of making a mucoadhesive drug delivery device of claim 37, wherein the one or more biocompatible solvents is water and the one or more mucoadhesive agents is glycerol.

39. The method of making a mucoadhesive drug delivery device of claim 37, wherein the one or more pharmacologically active agents are selected from the group consisting of peptides, antisense, anesthetics, analgesics, chemotherapy agents, antidiuretics, anti-inflammatories, neurotoxins and vitamins.

40. The method of making a mucoadhesive drug delivery device of claim 37, wherein the mucoadhesive device is processed into a form selected from the group consisting of a wafer, tablet, cylinder, sheet, particles or sphere.

* * * * *

SEQUENCE LISTING

```
<160> NUMBER OF SEQ ID NOS: 21

<210> SEQ ID NO 1
<211> LENGTH: 59
<212> TYPE: PRT
<213> ORGANISM: Artificial
<220> FEATURE:
<223> OTHER INFORMATION: synthetic construct similar to silk protein

<400> SEQUENCE: 1

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
                20                  25                  30

Gly Ala Gly Ser Gly Ala Gly Ala Gly Ser Gly Ala Gly Ala Gly Ser
            35                  40                  45

Gly Ala Gly Ala Gly Ser Gly Ala Ala Gly Tyr
        50                  55

<210> SEQ ID NO 2
<211> LENGTH: 6
<212> TYPE: PRT
<213> ORGANISM: Artificial
<220> FEATURE:
<223> OTHER INFORMATION: seq. repeated indefinitely, synthetic construct
      similar to silk protein

<400> SEQUENCE: 2

Gly Ala Gly Ala Gly Ser
1               5

<210> SEQ ID NO 3
<211> LENGTH: 71
<212> TYPE: PRT
<213> ORGANISM: Artificial
<220> FEATURE:
<223> OTHER INFORMATION: seq. repeated indefinitely, synthetic construct
      similar to silk protein containing RGD sequence from fibronectin.

<400> SEQUENCE: 3

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
                20                  25                  30

Gly Ala Gly Ser Gly Ala Gly Ala Gly Ser Gly Ala Gly Ala Gly Ser
            35                  40                  45

Gly Ala Gly Ala Gly Ser Gly Ala Ala Val Thr Gly Arg Gly Asp Ser
        50                  55                  60

Pro Ala Ser Ala Ala Gly Tyr
65                  70

<210> SEQ ID NO 4
<211> LENGTH: 74
<212> TYPE: PRT
<213> ORGANISM: Artificial
<220> FEATURE:
<223> OTHER INFORMATION: seq. repeated indefinitely, synthetic construct
      similar to silk protein containing sequence from laminin protein.

<400> SEQUENCE: 4
```

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Ala Pro Gly Ala Ser Ile Lys Val
    50                  55                  60

Ala Val Ser Ala Gly Pro Ser Ala Gly Tyr
65                  70

<210> SEQ ID NO 5
<211> LENGTH: 73
<212> TYPE: PRT
<213> ORGANISM: Artificial
<220> FEATURE:
<223> OTHER INFORMATION: seq. repeated indefinitely, synthetic construct
      similar to silk protein containing a different sequence from
      laminin protein.

<400> SEQUENCE: 5

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Ala Pro Gly Ala Ser Ile Lys Val
    50                  55                  60

Ala Val Ser Gly Pro Ser Ala Gly Tyr
65                  70

<210> SEQ ID NO 6
<211> LENGTH: 71
<212> TYPE: PRT
<213> ORGANISM: Artificial
<220> FEATURE:
<223> OTHER INFORMATION: seq. repeated indefinitely, synthetic construct
      similar to silk protein containing the RGD sequence from
      fibronectin.

<400> SEQUENCE: 6

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Arg Tyr Val Val Leu Pro Arg Pro Val Cys
    50                  55                  60

Phe Glu Lys Ala Ala Gly Tyr
65                  70

<210> SEQ ID NO 7
<211> LENGTH: 20
<212> TYPE: PRT
<213> ORGANISM: Artificial
<220> FEATURE:
<223> OTHER INFORMATION: seq. repeated indefinitely, synthetic construct
      similar to elastin protein.

<400> SEQUENCE: 7

Val Pro Gly Val Gly Val Pro Gly Val Gly Val Pro Gly Val Gly Val
1               5                   10                  15

Pro Gly Val Gly
            20

<210> SEQ ID NO 8
<211> LENGTH: 52
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 8

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
                20                  25                  30

Gly Val Pro Gly Val Gly Val Pro Gly Ala Gly Ala Gly Ser Gly Ala
            35                  40                  45

Gly Ala Gly Ser
        50

<210> SEQ ID NO 9
<211> LENGTH: 82
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 9

Gly Ala Ala Val Pro Gly Val Gly Val Pro Gly Val Gly Val Pro Gly
1               5                   10                  15

Val Gly Val Pro Gly Val Gly Val Ala Ala Gly Tyr Gly Ala Gly Ala
                20                  25                  30

Gly Ser Gly Ala Gly Ala Gly Ser Gly Ala Gly Ala Gly Ser Gly Ala
            35                  40                  45

Gly Ala Gly Ser Gly Ala Gly Ala Gly Ser Gly Ala Gly Ala Gly Ser
        50                  55                  60

Gly Ala Gly Ala Gly Ser Gly Ala Gly Ala Gly Ser Gly Ala Gly Ala
65                  70                  75                  80

Gly Ser

<210> SEQ ID NO 10
<211> LENGTH: 111
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 10

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
                20                  25                  30

Gly Ala Gly Ser Gly Ala Ala Gly Tyr Gly Ala Gly Ala Gly Ser Gly
            35                  40                  45

Ala Gly Ala Gly Ser Gly Ala Gly Ala Gly Ser Gly Ala Gly Ala Gly
        50                  55                  60

```
Ser Gly Ala Gly Ala Gly Ser Gly Val Gly Pro Gly Val Gly Val
 65                  70                  75                  80

Pro Gly Val Gly Val Pro Gly Val Gly Val Pro Gly Val Gly Val Pro
                 85                  90                  95

Gly Val Gly Val Pro Gly Val Gly Val Pro Gly Val Gly Val Pro
            100                 105                 110
```

<210> SEQ ID NO 11
<211> LENGTH: 88
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 11

```
Gly Val Gly Val Pro Gly Val Gly Val Pro Gly Val Gly Val Pro Gly
  1               5                  10                  15

Val Gly Val Pro Gly Val Gly Val Pro Gly Val Gly Val Pro Gly Val
             20                  25                  30

Gly Val Pro Gly Val Gly Val Pro Gly Ala Gly Ala Gly Ser Gly Ala
         35                  40                  45

Gly Ala Gly Ser Gly Ala Gly Ala Gly Ser Gly Ala Gly Ala Gly Ser
     50                  55                  60

Gly Ala Gly Ala Gly Ser Gly Ala Gly Ala Gly Ser Gly Ala Gly Ala
 65                  70                  75                  80

Gly Ser Gly Ala Gly Ala Gly Ser
                 85
```

<210> SEQ ID NO 12
<211> LENGTH: 108
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 12

```
Gly Val Gly Val Pro Gly Val Gly Val Pro Gly Val Gly Val Pro Gly
  1               5                  10                  15

Val Gly Val Pro Gly Val Gly Val Pro Gly Val Gly Val Pro Gly Val
             20                  25                  30

Gly Val Pro Gly Val Gly Val Pro Gly Val Gly Val Pro Gly Val Gly
         35                  40                  45

Val Pro Gly Val Gly Val Pro Gly Val Gly Val Pro Gly Ala Gly Ala
     50                  55                  60

Gly Ser Gly Ala Gly Ala Gly Ser Gly Ala Gly Ala Gly Ser Gly Ala
 65                  70                  75                  80

Gly Ala Gly Ser Gly Ala Gly Ala Gly Ser Gly Ala Gly Ala Gly Ser
                 85                  90                  95

Gly Ala Gly Ala Gly Ser Gly Ala Gly Ala Gly Ser
            100                 105
```

<210> SEQ ID NO 13
<211> LENGTH: 128
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 13

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Val Gly Val
    50                  55                  60

Pro Gly Val Gly Val Pro Gly Val Gly Val Pro Gly Val Gly Val Pro
65                  70                  75                  80

Gly Ala Gly Ala Gly Ser Gly Ala Gly Ala Gly Ser Gly Ala Gly Ala
                85                  90                  95

Gly Ser Gly Ala Gly Ala Gly Ser Gly Ala Gly Ala Gly Ser Gly Ala
            100                 105                 110

Gly Ala Gly Ser Gly Ala Gly Ala Gly Ser Gly Ala Gly Ala Gly Ser
        115                 120                 125

<210> SEQ ID NO 14
<211> LENGTH: 208
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 14

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Val Gly Val
    50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
                85                  90                  95

Val Gly Val Pro Gly Val Gly Val Pro Gly Val Gly Val Pro Gly Val
            100                 105                 110

Gly Val Pro Gly Val Gly Val Pro Gly Val Gly Val Pro Gly Val Gly
        115                 120                 125

Val Pro Gly Val Gly Val Pro Gly Val Gly Val Pro Gly Val Gly Val
    130                 135                 140

Pro Gly Val Gly Val Pro Gly Val Gly Val Pro Gly Val Gly Val Pro
145                 150                 155                 160

Gly Ala Gly Ala Gly Ser Gly Ala Gly Ala Gly Ser Gly Ala Gly Ala
                165                 170                 175

Gly Ser Gly Ala Gly Ala Gly Ser Gly Ala Gly Ala Gly Ser Gly Ala
            180                 185                 190

Gly Ala Gly Ser Gly Ala Gly Ala Gly Ser Gly Ala Gly Ala Gly Ser
        195                 200                 205

<210> SEQ ID NO 15
<211> LENGTH: 76
<212> TYPE: PRT
<213> ORGANISM: Artificial

<220> FEATURE:
<223> OTHER INFORMATION: seq. repeated indefinitely, synthetic construct
      similar to silk and elastin proteins.

<400> SEQUENCE: 15

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Ala Gly Ala Gly Ser Gly Ala
        35                  40                  45

Gly Ala Gly Ser Gly Ala Gly Ala Gly Ser Gly Ala Gly Ala Gly Ser
    50                  55                  60

Gly Ala Gly Ala Gly Ser Gly Ala Gly Ala Gly Ser
65                  70                  75

<210> SEQ ID NO 16
<211> LENGTH: 64
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 16

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Ala Gly Ala Gly Ser Gly Ala
        35                  40                  45

Gly Ala Gly Ser Gly Ala Gly Ala Gly Ser Gly Ala Gly Ala Gly Ser
    50                  55                  60

<210> SEQ ID NO 17
<211> LENGTH: 56
<212> TYPE: PRT
<213> ORGANISM: Artificial
<220> FEATURE:
<223> OTHER INFORMATION: seq. repeated indefinitely, synthetic construct
      similar to keratin protein.

<400> SEQUENCE: 17

Ala Lys Leu Lys Leu Ala Glu Ala Lys Leu Glu Leu Ala Glu Ala Lys
1               5                   10                  15

Leu Lys Leu Ala Glu Ala Lys Leu Glu Leu Ala Glu Ala Lys Leu Lys
            20                  25                  30

Leu Ala Glu Ala Lys Leu Glu Leu Ala Glu Ala Lys Leu Lys Leu Ala
        35                  40                  45

Glu Ala Lys Leu Glu Leu Ala Glu
    50                  55

<210> SEQ ID NO 18
<211> LENGTH: 15
<212> TYPE: PRT
<213> ORGANISM: Artificial
<220> FEATURE:
<223> OTHER INFORMATION: seq. repeated indefinitely, synthetic construct
      similar to collagen protein.

<400> SEQUENCE: 18

Gly Ala Pro Gly Pro Pro Gly Pro Pro Gly Pro Pro Gly Pro Pro
1               5                   10                  15

```
<210> SEQ ID NO 19
<211> LENGTH: 39
<212> TYPE: PRT
<213> ORGANISM: Artificial
<220> FEATURE:
<223> OTHER INFORMATION: seq. repeated indefinitely, synthetic construct
      similar to collagen protein.

<400> SEQUENCE: 19

Gly Ala Pro Gly Pro Pro Gly Pro Pro Gly Pro Pro Gly Pro Pro Gly
1               5                   10                  15

Ala Pro Gly Pro Pro Gly Pro Pro Gly Pro Pro Gly Pro Pro Gly Pro
            20                  25                  30

Ala Gly Pro Val Gly Ser Pro
        35

<210> SEQ ID NO 20
<211> LENGTH: 63
<212> TYPE: PRT
<213> ORGANISM: Artificial
<220> FEATURE:
<223> OTHER INFORMATION: seq. repeated indefinitely, synthetic construct
      similar to collagen protein with a cell binding domain from human
      collagen.

<400> SEQUENCE: 20

Gly Ala Pro Gly Pro Pro Gly Pro Pro Gly Pro Pro Gly Pro Pro Gly
1               5                   10                  15

Ala Pro Gly Pro Pro Gly Pro Pro Gly Pro Pro Gly Pro Pro Gly Leu
            20                  25                  30

Pro Gly Pro Lys Gly Asp Arg Gly Asp Ala Gly Pro Lys Gly Ala Asp
        35                  40                  45

Gly Ser Pro Gly Pro Ala Gly Pro Ala Gly Pro Val Gly Ser Pro
    50                  55                  60

<210> SEQ ID NO 21
<211> LENGTH: 15
<212> TYPE: PRT
<213> ORGANISM: Artificial
<220> FEATURE:
<223> OTHER INFORMATION: seq. repeated indefinitely, synthetic construct
      similar to collagen protein.

<400> SEQUENCE: 21

Gly Ala Pro Gly Ala Pro Gly Ser Gln Gly Ala Pro Gly Leu Gln
1               5                   10                  15
```